United States Patent
Caporini et al.

(10) Patent No.: US 12,000,915 B2
(45) Date of Patent: Jun. 4, 2024

(54) METHOD FOR CONDUCTING SOLID STATE NMR ON MACROMOLECULE-CONTAINING SOLID STATE FORMULATIONS

(71) Applicant: AMGEN INC., Thousand Oaks, CA (US)

(72) Inventors: Marc A. Caporini, Belmont, MA (US); Ron C. Kelly, Thousand Oaks, CA (US); Mariana De Maillé, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1 day.

(21) Appl. No.: 17/766,055

(22) PCT Filed: Oct. 2, 2020

(86) PCT No.: PCT/US2020/054018
§ 371 (c)(1),
(2) Date: Apr. 1, 2022

(87) PCT Pub. No.: WO2021/067762
PCT Pub. Date: Apr. 8, 2021

(65) Prior Publication Data
US 2022/0365156 A1    Nov. 17, 2022

Related U.S. Application Data

(60) Provisional application No. 62/909,918, filed on Oct. 3, 2019.

(51) Int. Cl.
*G01R 33/44*    (2006.01)
*G01N 24/08*    (2006.01)

(52) U.S. Cl.
CPC .......... *G01R 33/448* (2013.01); *G01N 24/08* (2013.01)

(58) Field of Classification Search
None
See application file for complete search history.

(56) References Cited

FOREIGN PATENT DOCUMENTS

| WO | WO-2008/119567 A2 | 10/2008 |
| WO | WO-2017/134140 A1 | 8/2017 |

OTHER PUBLICATIONS

"Different Molecular Motions in Lyophilized Protein Formulations as Determined by Laboratory and Rotating Frame Spin-Lattice Relaxation Times" by Yoshioka et al. (Year: 2002).*

(Continued)

*Primary Examiner* — Douglas X Rodriguez
(74) *Attorney, Agent, or Firm* — MARSHALL, GERSTEIN & BORUN LLP

(57) ABSTRACT

Disclosed herein is a method of conducting direct detection $^1$H solid state NMR ("ssNMR") on a macromolecule-containing solid state formulation. The method includes conducting a $^1$H spin-lattice relaxation time ("$T_1$") experiment on the solid state formulation at various temperatures to generate a $T_1$ value at each temperature, converting the $T_1$ values to $^1$H spin-lattice relaxation rate ("$R_1$"), and plotting $R_1$ versus temperature to generate a relaxation rate curve for the solid state formulation. The relaxation rate curve can be analyzed to determine the molecular mobility of the macromolecule in the solid state formulation, the degree of aggregation in the solid state formulation, and/or the stability of the solid state formulation.

20 Claims, 16 Drawing Sheets

(56) References Cited

OTHER PUBLICATIONS

"Solid-State Nuclear Magnetic Resonance Pharmaceutical Formulations" by Lubach et al. (Year: 2013).*
"Structural and Dynamic Properties of Amorphous Solid Dispersions: The Role of Solid-State Nuclear Magnetic Resonance Spectroscopy and Relaxometry" by Amrit et al. (Year: 2014).*
"Water Molecule Contributions to Proton Spin-Lattice Relaxation in Rotationally Immobilized Proteins" by Goddard et al. (Year: 2009).*
Cicerone et al., Beta-relaxation governs protein stability in sugar-glass matrices, Soft Matter, 8:2983-91 (2012).
Cicerone et al., Picosecond dynamic heterogeneity, hopping, and Johari-Goldstein relaxation in glass-forming liquids, Phys. Rev. Lett., 113(11):117801 (Sep. 2014).
Cory et al., Suppression of signals from the probe in bloch decay spectra, J. Magnetic Resonance, 80(1):128-32 (Oct. 1988).
Goddard et al., Water molecule contributions to proton spin-lattice relaxation in rotationally immobilized proteins, J. Magn. Reson., 199(1):68-74 (Jul. 2009).
International Application No. PCT/US2020/054018, International Search Report and Written Opinion, dated Jan. 25, 2021.
Lubach et al., Solid-state nuclear magnetic resonance of pharmaceutical formulations: Applications, Theory and Instrumentation, 18 pp., IN: Encyclopedia of Analytical Chemistry, Wiley, (2013).
Mensink et al., Influence of Miscibility of Protein-Sugar Lyophilizates on Their Storage Stability, AAPS J., 18(5):1225-32 (Sep. 2016).
Paudel et al., Structural and dynamic properties of amorphous solid dispersions: the role of solid-state nuclear magnetic resonance spectroscopy and relaxometry, J. Pharm. Sci., 103(9):2635-62 (Sep. 2014).
Yoshioka et al., Different molecular motions in lyophilized protein formulations as determined by laboratory and rotating frame spin-lattice relaxation times, J. Pharm. Sci., 91(10):2203-10 (Oct. 2002).
Fukushima et al., Experimental pulse NMR a nuts and bolts approach, Chapter III.D.2, First Edition, pp. 168-176 (1981).
European Patent Application No. 20793911.7, Communication Pursuant to Article 94(3) EPC, dated Apr. 10, 2024.

* cited by examiner

METHOD FOR CONDUCTING SOLID STATE NMR ON MACROMOLECULE-CONTAINING SOLID STATE FORMULATIONS

CROSS-REFERENCE TO RELATED APPLICATIONS

This application claims the benefit of priority of U.S. Provisional patent application No. 62/909,918, filed Oct. 3, 2019, the disclosure of which is hereby incorporated by reference in its entirety.

BACKGROUND

The present disclosure relates to methods of conducting solid state nuclear magnetic resonance ("ssNMR") spectroscopy on macromolecule-containing solid state formulations, such as antibody-containing pharmaceutical formulations that have been lyophilized or frozen, and using the methods disclosed herein to determine, for example, the stability of the formulation, the degree of aggregation in the formulation, and/or the degree of molecular mobility in the formulation.

Pharmaceutical formulations are often prepared in the solid state, such as frozen or lyophilized, to help preserve the integrity of the active pharmaceutical ingredient ("API") in the formulation during storage. Maintaining the stability of the API in the solid state is key for ensuring formulation quality. Current methods for understanding the stability of such a solid state formulation typically involve storing the solid state (e.g., lyophilized or frozen) formulation for a period of time, reconstituting or thawing the formulation to its liquid state, and then determining formulation stability using, for example, size exclusion chromatography ("SEC"). These liquid state stability studies are often time-consuming, resulting in delayed drug development and/or shorter-than-desired shelf life. Thus, there is a need to accurately determine the stability of a solid state formulation, such as a lyophilized or frozen pharmaceutical formulation, in real time to improve the time required for formulation development, and to reduce the risk of reformulation after years of development.

SUMMARY

In one aspect, the disclosure provides a method of conducting direct detection $^1$H solid state NMR ("ssNMR") on a macromolecule-containing solid state formulation, the method comprising: (a) equilibrating a solid state formulation comprising a macromolecule at a first temperature; (b) conducting a $^1$H spin-lattice relaxation time ("$T_1$") experiment on the solid state formulation at the first temperature using direct detection $^1$H ssNMR to generate at least three free induction decay ("FID") plots at the first temperature, wherein the $T_1$ experiment comprises a saturation recovery sequence having at least three variable delay times from which each FID plot is generated; (c) equilibrating the solid state formulation at a second temperature and repeating step (b) at the second temperature to generate at least three FID plots at the second temperature; (d) equilibrating the solid state formulation at a third temperature and repeating step (b) at the third temperature to generate at least three FID plots at the third temperature; (e) generating a saturation recovery curve at each temperature; and (f) fitting each saturation recovery curve to a nonlinear regression equation to generate a $T_1$ value at each temperature. In some cases, the method further comprises: (g) converting each $T_1$ value to $^1$H spin-lattice relaxation rate ("$R_1$"), and (h) plotting $R_1$ versus temperature to generate a relaxation rate curve for the solid state formulation. In some embodiments, the method further comprises analyzing the relaxation rate curve to determine the molecular mobility of the macromolecule in the solid state formulation, the degree of aggregation in the solid state formulation, and/or the stability of the solid state formulation. In various embodiments, the $T_1$ experiment comprises baseline suppression. In various cases, the $T_1$ experiment comprises magic angle spinning. In some cases, the method excludes one or both of retuning and recalibrating the ssNMR probe after equilibrating at the first temperature.

In some cases, step (d) is repeated at 5 or more additional temperatures. In some embodiments, step (d) is repeated at 10 or more additional temperatures. In various cases step (d) is repeated at 25 or more additional temperatures.

In some embodiments, each temperature is in a range from about −200° C. to about 150° C. In various embodiments, each temperature is in a range from about −100° C. to about 150° C. In some cases, each temperature is in a range from about −50° C. to about 150° C. In various cases, the highest and lowest temperatures have a difference of at least about 25° C. In some embodiments, the lowest temperature is in a range from about −200° C. to about 25° C. In various embodiments, the lowest temperature is in a range from about −100° C. to about 0° C. In some cases, the lowest temperature is in a range from about −50° C. to about −30° C.

In various cases, in each equilibrating step the solid state formulation is held at the temperature for a duration in the range of about one minute to about one hour before conducting the $T_1$ experiment. In some embodiments, in each equilibrating step the solid state formulation is held at the temperature for a duration in the range of about one minute to about 10 minutes before conducting the $T_1$ experiment. In various embodiments, the solid state formulation is held at the temperature for about five minutes before conducting the $T_1$ experiment.

In some cases, each $T_1$ experiment comprises at least five variable delay times at each temperature to generate at least five FID plots at each temperature. In some embodiments, each $T_1$ experiment comprises at least six variable delay times at each temperature to generate at least six FID plots at each temperature. In various cases, each $T_1$ experiment comprises at least eight variable delay times at each temperature to generate at least eight FID plots at each temperature. In some embodiments, each $T_1$ experiment comprises at least nine variable delay times at each temperature to generate at least nine FID plots at each temperature.

In some embodiments, the saturation recovery curve is generated by: (a) plotting the signal intensity of each of the at least three FID plots versus delay time; or (b) Fourier transforming each of the at least three FID plots to generate a plot of intensity versus frequency; and (i) plotting peak height versus delay time; or (ii) plotting integral peak intensity versus delay time. In various embodiments, the saturated recovery curve is generated by plotting the signal intensity of the FID plot versus delay time.

In some cases, the $T_1$ experiment comprises a magnetic field having a frequency in a range from about 200 MHz to about 1.2 GHz. In various cases, the frequency range is from about 300 MHz to about 1 GHz. In various embodiments, the frequency is about 500 MHz.

In some embodiments, all of the $T_1$ experiments are conducted within a time period of up to 48 hours. In various embodiments, all of the $T_1$ experiments are conducted within a time period of up to 24 hours. In some cases, all of the $T_1$ experiments are conducted within a time period of up to 12 hours. In various cases, all of the $T_1$ experiments are conducted within a time period of up to 6 hours.

In some embodiments, the macromolecule is a biologic molecule. In various embodiments, the biologic molecule is a protein. In some cases, the protein is an antibody or a bispecific antibody construct.

In various cases, the solid state formulation is a lyophilized formulation. In some embodiments, the fitting of step (f) is monoexponential. In various embodiments, the highest temperature is in a range from about 50° C. to about 150° C. In some cases, the highest temperature is in a range from about 100° C. to about 150° C. In various cases, the highest and lowest temperatures have a difference of at least about 50° C. In some embodiments, the $T_1$ experiment comprises a variable delay period in a range from about 0.01 seconds to about 60 seconds.

In some cases, the solid state formulation is a frozen formulation. In various cases, the fitting of step (f) is biexponential. In some embodiments, the highest temperature is from about −15° C. to about 0° C. In some embodiments, the highest temperature is from about −15° C. to about −10° C. In some cases, the highest and lowest temperatures have a difference of at least about 40° C. In some embodiments, each $T_1$ experiment comprises nine variable delay times at each temperature to generate nine FID plots at each temperature. In various cases, $T_1$ experiment comprises a variable delay period in a range from about 0.1 seconds to about 240 seconds.

The method of claim 1, wherein the solid state formulation is a lyophilized formulation and: the saturation recovery curve is generated by plotting the signal intensity of each of the at least three FID plots versus delay time; the $T_1$ experiment comprises baseline suppression and magic angle spinning; steps (d)-(f) are repeated at 15 or more temperatures; each temperature is in a range from about −50° C. to about 150° C.; the highest and lowest temperatures have a difference from about 75° C. to about 100° C.; in each equilibrating step the solid state formulation is held at the temperature for a duration in the range of about one minute to about ten minutes before conducting the $T_1$ experiment; the method excludes retuning and recalibrating the ssNMR probe after equilibrating at the first temperature; the variable delay period is in a range from about 0.1 seconds to about 60 seconds; and each T1 experiment comprises six variable delay times at each temperature to generate six FID plots at each temperature. In some embodiments, the method further comprises: (g) converting each $T_1$ value to $^1H$ spin-lattice relaxation rate ("$R_1$"), and (h) plotting $R_1$ versus temperature to generate a relaxation rate curve for the solid state formulation. In various embodiments, the method further comprises analyzing the relaxation rate curve to determine the molecular mobility of the macromolecule in the solid state formulation, the degree of aggregation in the solid state formulation, and/or the stability of the solid state formulation. In some cases, the macromolecule is a biologic molecule. In various cases, the biologic molecule is a protein.

The method of claim 1, wherein the solid state formulation is a frozen formulation and: the saturation recovery curve is generated by plotting the signal intensity of each of the at least three FID plots versus delay time; the $T_1$ experiment comprises baseline suppression and magic angle spinning; steps (d)-(f) are repeated at 25 or more temperatures; each temperature is in a range from about −50° C. to about 0° C.; the highest and lowest temperatures have a difference from about 25° C. to about 40° C.; in each equilibrating step the solid state formulation is held at the temperature for a duration in the range of about one minute to about ten minutes before conducting the $T_1$ experiment; the method excludes retuning and recalibrating the ssNMR probe after equilibrating at the first temperature; the variable delay period is in a range from about 0.01 seconds to about 240 seconds; and each $T_1$ experiment comprises nine variable delay times at each temperature to generate nine FID plots at each temperature. In some embodiments, the method further comprises: (g) converting each $T_1$ value to $^1H$ spin-lattice relaxation rate ("$R_1$"), and (h) plotting $R_1$ versus temperature to generate a relaxation rate curve for the solid state formulation. In various embodiments, the method further comprises analyzing the relaxation rate curve to determine the molecular mobility of the macromolecule in the solid state formulation, the degree of aggregation in the solid state formulation, and/or the stability of the solid state formulation. In some cases, the macromolecule is a biologic molecule. In various cases, the biologic molecule is a protein.

Another aspect of the disclosure provides a method of selecting a macromolecule-containing solid state formulation among a group of test macromolecule-containing solid state formulations, the method comprising: (I) generating a relaxation rate curve for each macromolecule-containing solid state formulation in the group of test macromolecule-containing solid state formulations; wherein the relaxation rate curve for each macromolecule-containing solid state formulation is generated by: (a) equilibrating the solid state formulation at a first temperature; (b) conducting a $^1H$ spin-lattice relaxation time ("$T_1$") experiment on the solid state formulation at the first temperature using direct detection $^1H$ ssNMR to generate at least three free induction decay ("FID") plots at the first temperature, wherein the $T_1$ experiment comprises a saturation recovery sequence having at least three variable delay times from which each FID plot is generated; (c) equilibrating the solid state formulation at a second temperature, and repeating step (b) at the second temperature to generate at least three FID plots at the second temperature; (d) equilibrating the solid state formulation at a third temperature and repeating step (b) at the third temperature to generate at least three FID plots at the third temperature; (e) generating a saturation recovery curve at each temperature; (f) fitting each saturation recovery curve to a nonlinear regression equation to generate a $T_1$ value at each temperature; (g) converting each $T_1$ value to $^1H$ spin-lattice relaxation rate ("$R_1$"), and (h) plotting $R_1$ versus temperature to generate a relaxation rate curve for the solid state formulation; (II) comparing the maximum $R_1$ peak value of each curve, the temperature of the maximum $R_1$ peak of each curve, the width of the maximum $R_1$ peak of each curve, or a combination thereof; and (III) selecting the solid state formulation which has the lowest maximum $R_1$ peak value, the highest temperature of the maximum $R_1$ peak, or the narrowest $R_1$ peak width.

Yet another aspect of the disclosure provides a method of selecting a formulation excipient for use in a macromolecule-containing solid state formulation, the method comprising: (I) generating a relaxation rate curve for each macromolecule-containing solid state formulation in a group of test macromolecule-containing solid state formulations, each formulation having a different composition of excipients, a different amount of one or more excipients, or both; wherein the relaxation rate curve for each macromolecule-containing solid state formulation is generated by: (a) equilibrating the solid state formulation at a first temperature; (b) conducting a $^1H$ spin-lattice relaxation time ("$T_1$") experiment on the solid state formulation at the first temperature using direct detection $^1$H ssNMR to generate at least three free induction decay ("FID") plots at the first temperature, wherein the $T_1$ experiment comprises a saturation recovery sequence having at least three variable delay times from which each FID plot is generated; (c) equilibrating the solid state formulation at a second temperature, and repeating step (b) at the second temperature to generate at least three FID plots at the second temperature; (d) equilibrating the solid state formulation at a third temperature, and repeating step (b) at the third temperature to generate at least three FID plots at the third temperature; (e) generating a saturation recovery curve at each temperature; (f) fitting each saturation recovery curve to a nonlinear regression equation to generate a $T_1$ value at each temperature; (g) converting each $T_1$ value to $^1$H spin-lattice relaxation rate ("$R_1$"), and (h) plotting $R_1$ versus temperature to generate a relaxation rate curve for the solid state formulation; (II) comparing the maximum $R_1$ peak value of each curve, the temperature of the maximum $R_1$ peak of each curve, the width of the maximum $R_1$ peak of each curve, or a combination thereof; and (III) selecting an excipient that is present in the solid state formulation that has the lowest maximum $R_1$ peak value, the highest temperature of the maximum $R_1$ peak, or the narrowest $R_1$ peak width.

Further aspects and advantages will be apparent to those of ordinary skill in the art from a review of the following detailed description. While the methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
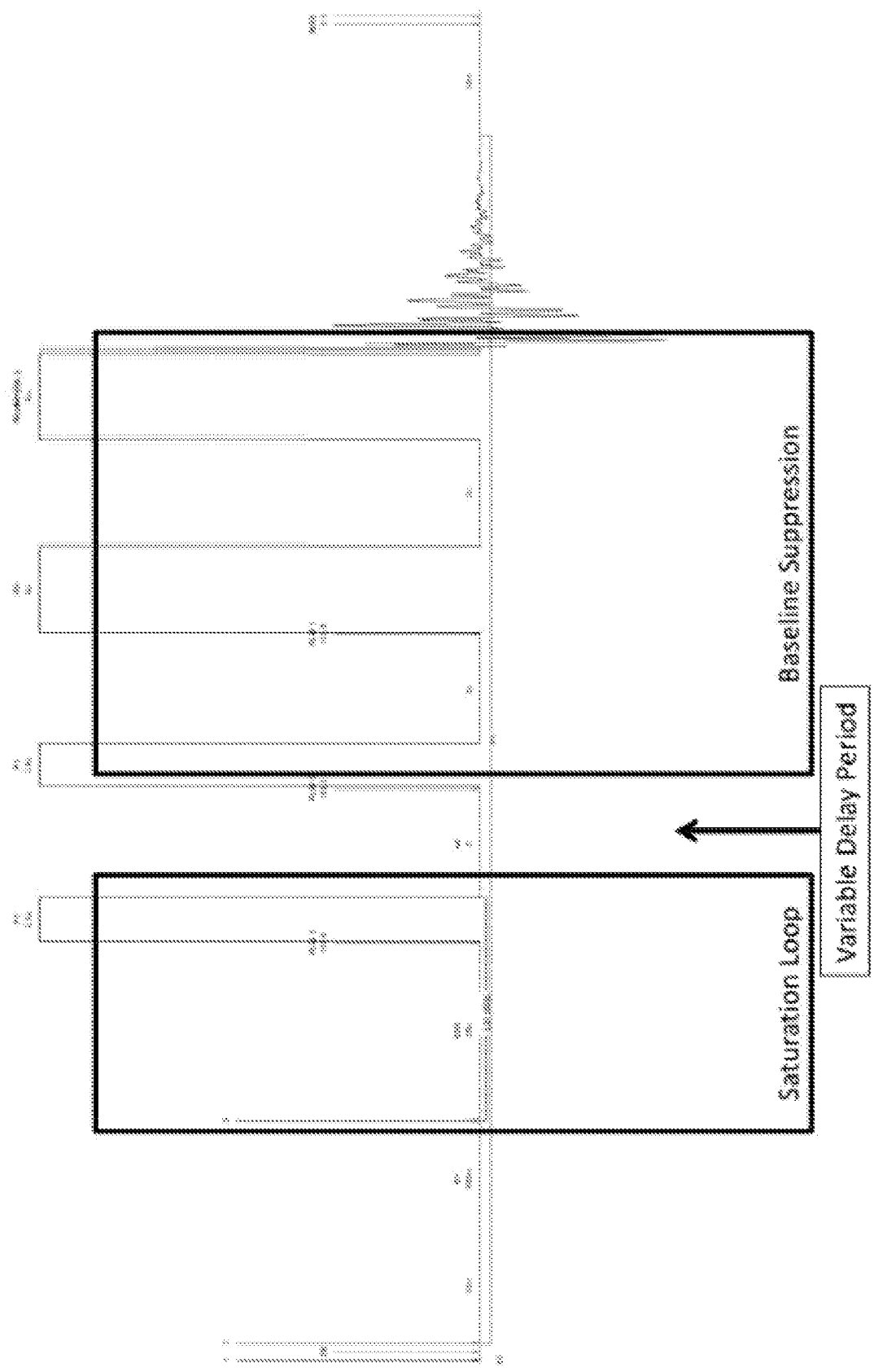
FIG. 1 shows the pulse sequence for the ssNMR methods of the disclosure including the baseline suppression sequence.

Described herein are methods of conducting direct detection $^1$H solid state nuclear magnetic resonances ("ssNMR") on a macromolecule-containing solid state formulation. The methods include conducting a $^1$H spin-lattice relaxation time ("$T_1$") experiment on the solid state formulation over a range of temperatures to generate a series of $T_1$ values. As used herein, "$T_1$ relaxation" refers to the process of establishing (or re-establishing) the normal Boltzmann population distribution of α and β spin states in the magnetic field after application of a radio frequency ("Rf") pulse. The $T_1$ values can be converted to $^1$H spin-lattice relaxation rate ("$R_1$") values, which can be plotted versus temperature to generate a relaxation rate curve for the solid state formulation. The relaxation rate curve can be analyzed to determine the molecular mobility of the macromolecule in the solid state formulation and/or the degree of aggregation in the solid state formulation. Thus, the methods described herein can act as a proxy for determining the stability of a solid state formulation.

The ssNMR methods of the disclosure advantageously provide detailed information about the stability of macromolecule-containing solid state formulations, allowing adjustment and optimization of the formulations to maximize formulation stability on a reasonable time scale. For example, the methods described herein provide information about how various small changes in the molecular structure of a compound, such as a biologic drug, can lead to increased or decreased molecular motion and aggregation in a formulation. The methods also provide knowledge about whether such motional changes are due to the compounds in the formulation, such as an active pharmaceutical ingredient ("API"), or the formulation itself, by comparing the generated measurements with those from a placebo (i.e., a formulation comprising exactly the same components as the test formulation at the same concentration, but without the API). Further, the methods described herein can show how substituting, adding and/or removing formulation excipients can affect molecular motion, and thus, aggregation and stability. The methods described herein also provide understanding about how processing conditions (e.g., freezing rate, annealing, or primary/secondary drying) can impact formulation stability.

The methods disclosed herein are a significant advancement in the characterization of compounds, such as biologic drugs, in complex solid state formulations. Although some small angle neutron scattering ("SANS") experiments have shown the potential to yield similar information, these experiments require weeks of experimental time at a National Institute of Standards and Technology ("NIST") facility, for example, for a single sample, and are thus, difficult and time-consuming. In contrast, the methods described herein can be completed in far shorter time frames—about 20 minutes per temperature, and about 1 day to measure a range of temperatures for a particular sample. The ability to accurately predict formulation stability based on molecular mobility measurements at time zero (without the need for stability studies) in the solid state (e.g., frozen or lyophilized) significantly expedites formulation development and also reduces the risk of requiring reformulation after years of development.

The methods disclosed herein allow the measurement of the molecular mobility of compounds (e.g., biologics) in the solid state (e.g., lyophilized or frozen) using ssNMR. These ssNMR measurements can be correlated with compound aggregation, and thus, formulation stability. Reports in the literature describe the correlation of $^1$H NMR relaxation in the solid state to aggregation rates in lyophilized proteins. See, e.g., Mensink et al., AAPS J 18(5):1225-32 (2016). Other reports have shown that protein degradation in the solid state is a diffusion process that is gated by fast molecular motions in the ps-ns timescale (β relaxation) (see Cicerone et al., Physical Review Letters 113:117801 (2014) and Cicerone and Douglas, Soft Matter 8:2983-2991 (2012)), such that:

$$\log(\tau_{deg}) \propto \log(\tau_{\beta JG}) \propto 1/\langle u^2 \rangle$$

where, $\tau_{deg}$ and $\tau_{\beta JG}$ are the inverse rates of protein degradation and beta-relaxation, respectively, and $\langle u^2 \rangle$ is the mean-squared displacement from SANS backscattering measurements. ssNMR relaxation rates are also sensitive probes of motions in the ps-ns range and yield similar molecular mobility information, therefore the equation, above, can be extended to:

$$\log(\tau_{deg}) \propto \log(\tau_{\beta JG}) \propto 1/\langle u^2 \rangle \propto \log(T_1) \propto \log(1/R_1)$$

Thus, in general, longer $T_1$ relaxation times indicate less molecular mobility. In other words, the less molecular motion of a compound, such as a biologic, in a solid state formulation, the longer the ssNMR $T_1$, and the greater the stability of the solid state formulation.

The methods described herein are a significant advancement over traditional ssNMR methods for determining the mobility of macromolecules in the solid state. Traditional methods rely on measuring $^1$H relaxation using cross polarization to $^{13}$C NMR. Cross polarization is typically used in solid state NMR of macromolecules because the $^{13}$C spectrum affords better resolution, allowing one to distinguish the peaks of a larger compound, such as a biologic, from those resulting from excipients. The drawback of the cross polarization method is that the sensitivity is low due to the about 1% natural abundance of $^{13}$C. As a consequence, $^{13}$C NMR has very low sensitivity requiring signal averaging over long acquisition times, resulting in low throughput (e.g., days to a week, per $^1$H relaxation measurement, per sample). In addition, the cross polarization method is limited to formulations with compound (e.g., biologic) concentrations of closer 5% or more (by mass) due to sensitivity limitations.

In contrast, the methods described herein detect the $^1$H $T_1$ relaxation directly on the $^1$H, which results in vastly improved sensitivity and throughput of over 100-fold. The directly detected $^1$H $T_1$ relaxation was found to trend similarly to the $^{13}$C detected for solid state formulations, such as lyophilized and frozen formulations. As a consequence, the methods described herein allow a single relaxation measurement to be done in much shorter time periods (e.g., about 20 minutes). This added throughput enables the collection of $^1$H $T_1$ measurements over a range of temperatures (limited only by the specifications of the NMR equipment) to yield relaxation rates versus temperature. These relaxation profiles can be fit using standard NMR relaxation equations, based on molecular motions, with some modifications. Fitting these relaxation profiles to motional modes allows the comparison of various samples in terms of the frequency, amplitude, and activation energy (or temperature) of the underlying molecular motions. Thus, the methods provided herein, which provide knowledge about the relaxation rate versus temperature of a solid state formulation, greatly increases the information content that can be gleaned about solid state formulations compared to traditional methods. In fact, the information about molecular motions in solid formulations generated using the methods provided herein offers an unprecedented window into the molecular level interactions that govern stability of the formulations, and is the first time such an analysis has been performed on such complicated systems in this manner. As previously described, the motional changes that can be observed using the methods described herein (ssNMR relaxation measurements) correlate well with known aggregation behavior of compounds in solid state formulations, such as lyophilized antibodies and frozen formulations containing bispecific antibody constructs. Thus, the methods described herein allow the attribution of certain motional changes in solid formulations to changes in compound structure (e.g., bispecific antibody constructs, for example, by adding an intra-domain disulfide bridge in a binding domain), or to interactions between excipients and the compound (e.g., benzyl alcohol can be shown to restrict motion in certain bispecific antibody constructs leading to reduced aggregation).

Thus, disclosed herein is a method of conducting direct detection $^1$H ssNMR on a macromolecule-containing solid state formulation. The method disclosed herein comprises: (a) equilibrating a solid state formulation comprising a macromolecule at a first temperature; (b) conducting a $^1$H spin-lattice relaxation time ("$T_1$") experiment on the solid state formulation at the first temperature using direct detection $^1$H ssNMR to generate at least three free induction decay ("FID") plots at the first temperature, wherein the $T_1$ experiment comprises a saturation recovery sequence having at least three variable delay times from which each FID plot is generated; (c) equilibrating the solid state formulation at a second temperature, and repeating step (b) at the second temperature to generate at least three FID plots at the second temperature; (d) equilibrating the solid state formulation at a third temperature, and repeating step (b) at the third temperature to generate at least three FID plots at the third temperature; (e) generating a saturation recovery curve at each temperature; and (f) fitting each saturation recovery curve to a nonlinear regression equation to generate a $T_1$ value at each temperature. In some embodiments, the method further comprises: (g) converting each $T_1$ value to $^1$H spin-lattice relaxation rate ("$R_1$"); and (h), plotting $R_1$ versus temperature to generate a relaxation rate curve for the solid state formulation.

As used herein "solid state nuclear magnetic resonance" or "ssNMR" refers to NMR conducted on a sample in the solid state, as described above, in which anisotropic interactions are present. As used herein, direct detection $^1$H ssNMR refers to detecting $^1$H $T_1$ directly on an excited $^1$H, as opposed to, e.g., $^{13}$C cross-polarization, in which $^1$H is excited but transfers its energy to $^{13}$C for $T_1$ detection. As used herein, "spin-lattice relaxation time" or "$T_1$" refers to the time it takes for a sample to return to 63% of its equilibrium value after excitation with a radio frequency ($R_f$) pulse. $T_1$ is an exponential process. As used herein, "$^1$H spin-lattice relaxation time experiment" or "$T_1$ experiment" refers to a method for determining the $T_1$ of a sample, such as a saturation recovery sequence and an inversion recovery sequence. As used herein, "saturation recovery" or "saturation recovery sequence" refers to a method of determining $T_1$ in which a sample is subjected to multiple $R_f$ pulses (e.g., 90 degree pulses) at short delay times. As used herein, "free induction decay" or "FID" refers to a time domain signal generated by a $T_1$ experiment. The FID is produced by induction from the motion of magnetic moments of nuclei and decays with time. A "free induction decay plot" or "FID plot" refers to a plot of the emitted radio intensity as a function of time. As used herein, "variable delay time" refers to the duration of time during which the magnetization relaxes by spin-lattice ("$T_1$") relaxation and is tipped into the transverse plane by the pulse (e.g., the 90° pulse). As used herein, "$^1$H spin-lattice relaxation rate" or "$R_1$", refers to the rate at which a sample returns to its equilibrium after excitation with a radio frequency ($R_f$) pulse. Thus, $R_1=1/T_1$, where $T_1$ is the time it takes for the magnetization to return to 63% of its equilibrium value.

In some cases, the method further comprises repeating step (d) at additional temperatures. In some cases, each successive $T_1$ experiment is conducted at a temperature higher than the temperature of the previous $T_1$ experiment. The $T_1$ experiment can be conducted at a number of temperatures that allow the formation of a curve when plotting relaxation rate versus temperature. In some embodiments, the $T_1$ experiment is conducted at 5 or more additional temperatures. In various embodiments, the $T_1$ experiment is conducted at 10 or more temperatures. In some cases, the $T_1$ experiment is conducted at 15 or more temperatures. In various cases, the $T_1$ experiment is conducted at 20 or more temperatures. In some embodiments, the $T_1$ experiment is conducted at 25 or more temperatures. In various cases, the $T_1$ experiment is conducted at 30 or more, 35 or more, 40 or more, 45 or more, 50 or more, 55 or more, 60 or more, 65 or more, 70 or more, or 75 or more temperatures. In various embodiments the $T_1$ experiment is conducted at 100 or less temperatures, such as 95 or less, 90 or less, 85 or less, 80 or less, 75 or less, 70 or less, 65 or less, 60 or less, 55 or less, 50 or less temperatures, 45 or less, 40 or less, 35 or less, or 30 or less temperatures. In some cases, the $T_1$ experiment is conducted at 25 or less, 20 or less, 15 or less, 10 or less, or 5 or less temperatures.

The solid state formulation sample is equilibrated at each temperature before conducting the $T_1$ experiment at that temperature. In some embodiments, the solid state formulation is held at each temperature for a duration in the range of about one minute to about one hour. In various embodiments, the solid state formulation is held at each temperature for a duration in the range of about one minute to about 30 minutes. In some embodiments, the solid state formulation is held at each temperature for a duration in the range of about one minute to about ten minutes. In various embodiments, the solid state formulation is held at each temperature for a duration in the range of about one minute to about five minutes. In some embodiments, the solid state formulation is held at each temperature for a time selected from the group consisting of 1, 2, 3, 4, 5, 6, 7, 8, 9, and 10 minutes before conducting each $T_1$ experiment. For example, the solid state formulation can be held at each temperature for about 5 minutes before conducting each $T_1$ experiment.

$T_1$ Experiment

The method disclosed herein comprises conducting $T_1$ experiments using a saturation recovery sequence over various temperatures to generate a $T_1$ value at each temperature. In some embodiments, the $T_1$ experiment is conducted with baseline suppression. FIG. 1 shows a saturation recovery pulse sequence of the disclosure with baseline suppression. As previously described, $^{13}$C ssNMR affords better resolution than $^1$H ssNMR, but has low sensitivity, which results in low throughput. Using baseline suppression as the detection method in direct detection $^1$H ssNMR (instead of, for example, direct large window, direct narrow window, cross polarization, or DUMBO) generates $^1$H ssNMR results that are the most similar to results that would be generated using $^{13}$C ssNMR. See, e.g., Example 1 and FIGS. 2-5. Further, incorporating baseline suppression into the $T_1$ measurement, along with saturation recovery, is advantageous in that it removes the requirement of retuning the probe and recalibrating pulses at the various temperatures. Advantageously, 1H ssNMR can be conducted on a sample at various temperatures without tuning the probe or recalibrating the instrument between temperatures, allowing for high throughput of samples. Thus, in some embodiments, the method disclosed herein excludes retuning and/or recalibrating the ssNMR probe after the solid state sample is equilibrated at the first temperature.

In various embodiments, the $T_1$ experiment comprises a magic angle spinning. As used herein, "magic angle spinning" refers to the technique in ssNMR in which artificial motion is introduced by placing the axis of the ssNMR sample rotor at an angle of about 54.7° with respect to magnetic field strength to remove or reduce the influence of anisotropic interactions, thereby increasing spectral resolution. In some embodiments, the magic angle spinning has a frequency in a range from about 2 kHz to about 16 kHz. In some cases, the frequency of the magic angle spinning is about 8 kHz.

In some cases, the $T_1$ experiment comprises a magnetic field having a frequency in a range from about 200 MHz to about 1.2 GHz. In various cases, the magnetic field has a frequency in a range from about 300 MHz to about 1.0 GHz. In some cases, the magnetic field has a frequency of about 300 MHz. In some embodiments, the magnetic field has a frequency of about 750 MHz. In various embodiments, the magnetic field has a frequency of about 500 MHz. In some embodiments, the magnetic field has a frequency of about 1.0 GHz.

The temperature range over which the $T_1$ experiment is conducted can depend on the properties of the specific solid state sample, such as the type of solid state sample (e.g., frozen or lyophilized) and the melting point of the solid state sample. In some embodiments, the $T_1$ experiment is conducted at the lowest temperature the solid state formulation can reasonably achieve to record an initial $T_1$. In some cases, the lowest temperature of the $T_1$ experiment is in a range from about −200° C. to about 25° C. In various cases, the lowest temperature is in range from about −100° C. to about 0° C., or from about −100° C. to about −50° C. In some embodiments, the lowest temperature is in a range from about −50° C. to about −30° C. In various embodiments, the lowest temperature is in a range from about −30° C. to about 0° C. In various embodiments, the lowest temperature is in a range from about 0° C. to about 25° C. The sample is then heated and the $T_1$ experiment is conducted at additional temperatures. In some cases, the highest temperature at which a $T_1$ experiment is conducted is the glass transition temperature (Tg) or melting temperature of the solid state formulation. In some cases, the highest temperature at which a $T_1$ experiment is conducted in a range from about 0° C. to about 150° C. In various cases, the highest temperature is in range from about 75° C. to about 150° C., or from about 100° C. to about 150° C., or from about 50° C. to about 100° C., or from about 75° C. to about 100° C. In some embodiments, the highest temperature is in a range from about 0° C. to about 50° C., or from about 10° C. to about 50° C., or from about 10° C. to about 30° C., or from about 0° C. to about 25° C. In some embodiments, the $T_1$ experiments are conducted over a temperature range from about −200° C. to about 150° C. In various cases, the temperature range is from about −100° C. to about 150° C. In some embodiments, the temperature range is from about −50° C. to about 150° C., or from about −50° C. to about 80° C. In some embodiments, the highest and lowest temperatures have a difference of at least about 10° C. In some embodiments, the highest and lowest temperatures have a difference of at least about 15° C. In various embodiments, the highest and lowest temperatures have a difference of at least about 20° C. In various cases, the highest and lowest temperatures have a difference of at least about 25° C. In some embodiments, the highest and lowest temperature have a difference in a range from about 25° C. to about 40° C. In various embodiments, the highest and lowest temperature have a different in a range from about 75° C. to about 100° C. In some cases, the highest and lowest temperatures have a difference of about 10° C., or about 15° C., or about 20° C., or about 25° C., or about 30° C., or about 35° C., or about 40° C., or about 45° C., or about 50° C., or about 55° C., or about 60° C., or about 65° C., or about 70° C., or about 75° C., or about 80° C., or about 85° C., or about 90° C., or about 95° C., or about 100° C., or about 110° C., or about 120° C., or about 130° C., or about 140° C., or about 150° C.

The $T_1$ experiment comprises a saturation recovery sequence having at least three variable delay times from which each FID plot is generated. In various embodiments, the saturation recovery pulse sequence can be represented as shown in the schematic of FIG. 1. In some embodiments, the saturation recovery sequence comprises at least four, or at least five, or at least six, or at least seven, or at least eight, or at least nine, or at least ten variable delay times from which each FID plot is generated. In various embodiments, the $T_1$ experiment comprises three variable delay times at each temperature to generate three FID plots at each temperature. In various embodiments, the $T_1$ experiment comprises five variable delay times at each temperature to generate five FID plots at each temperature. In some cases, the $T_1$ experiment comprises six variable delay times at each temperature to generate six FID plots at each temperature. In various cases, the $T_1$ experiment comprises eight variable delay times at each temperature to generate eight FID plots at each temperature. In various cases, the $T_1$ experiment comprises nine variable delay times at each temperature to generate nine FID plots at each temperature. In some embodiments the variable delay time period ranges from about 0.01 seconds to about 10 minutes. In various embodiments the variable delay time period ranges from about 0.01 seconds to about 5 minutes. In some cases, the variable delay time is no more than about 10 minutes, or about 9 minutes, or about 8 minutes, or about 7 minutes, or about 6 minutes, or about 5 minutes, or about 4 minutes. In some cases, the variable delay time is no more than 240 seconds. In various cases, the variable delay time is no more than 300 seconds. The FID plots that are generated by the $T_1$ experiments can be used to generate a saturation recovery curve for each temperature.

As previously described, the methods of the disclosure detect the $^1H$ $T_1$ relaxation directly on the $^1H$, which results in vastly improved sensitivity and throughput. Thus, in some embodiments, all of the $T_1$ experiments are conducted within a time period of up to 72 hours. In various embodiments, all of the $T_1$ experiments are conducted within a time period of up to 60 hours. In some cases, all of the $T_1$ experiments are conducted within a time period of up to 48 hours. In various cases, all of the $T_1$ experiments are conducted within a time period of up to 24 hours. In some embodiments, all of the $T_1$ experiments are conducted within a time period of up to 12 hours. In various embodiments, all of the $T_1$ experiments are conducted within a time period of up to 6 hours, or up to 5 hours, or up to 4 hours, or up to 3 hours, or up to 2 hours, or up to 1 hour.

Saturation Recovery Curve

A saturation recovery curve can be generated for each temperature at which the $T_1$ experiment is conducted. In some embodiments, the saturation recovery curve can be generated by plotting the signal intensity of each of the at least three FID plots that result from the $T_1$ experiments versus delay time. The maximum magnitude of the FID, which is equivalent to the area under the curve for the entire spectrum, can be used as the signal intensity, where the magnitude for each time point z in the FID is calculated by $r=|z|=\sqrt{a^2+b^2}$, where $z=a+bi$ is a complex data point, and then the maximum is found over the set of magnitudes for an FID. Generating the saturation recovery curve using maximum magnitude allows for superior and more consistent curve fitting because the method does not require proper phasing of hard-to-phase broad peaks to result in good peak integration. In various embodiments, the saturation recovery curve at each temperature is generated by subjecting the FID plot to Fourier transform, which results in a plot of intensity versus frequency, and then plotting either the peak height versus delay time or the integrated peak intensity versus delay time. As used herein, "integrated peak intensity" refers to the area under the curve for one or more peaks in the ssNMR spectrum that have been properly phased.

The saturation recovery curve that is generated at each temperature can be fit using a nonlinear regression equation to generate a $T_1$ value for each temperature. The curve fitting equation used to determine $T_1$ depends on the type of solid state formulation. If the solid state formulation is a monophasic, such as a purely amorphous lyophilized formulation, then a monoexponential curve fitting equation can be used. If the solid state formulation is biphasic, such as a frozen formulation with some crystalline ice and some amorphous freeze concentrate (e.g., excipients and API) or a crystalline/amorphous lyophilized formulation (i.e. crystalline mannitol and amorphous sucrose and API), then a biexponential curve fitting equation can be used. A frozen formulation can be fit using a biexponential equation because a frozen formulation includes both ice and freeze concentrate (which is everything except the ice), each of which has a separate relaxation profile requiring a separate fit.

Monoexponential curve fitting can be accomplished by standard techniques known in the art. For example, any nonlinear regression fitting routine can be used to fit saturation recovery curves to the equation $I(t)=I_0(1-e^{-t/T_1})$, where $I(t)$ is the signal intensity at delay time t, and $I_0$ and $T_1$ are fit parameters representing the intensity and relaxation time.

Biexponential curve fitting can be accomplished by standard techniques known in the art. For example, any nonlinear regression fitting routine can be used to fit saturation recovery curves to the equation $I(t)=I_{0,a}(1-e^{-t/T_{1,a}})+I_{0,b}(1-e^{-t/T_{1,b}})$, where I(t) is the signal intensity at delay time t, and $I_{0,a}$, $T_{1a}$ and $I_{0,b}$, $T_{1b}$ are fit parameters representing the intensity and relaxation times of phases a and b in the biphasic formulation.

Solid State Formulation

The solid state formulation of the disclosure can be any solid state formulation that comprises a macromolecule. As used herein, "solid state formulation" refers to a formulation that is in solid form, such that the atoms and molecules of the formulation occupy fixed positions with respect to one another. The solid form can be crystalline or amorphous (e.g., a gel or a thin film). In various embodiments, the solid state formulation can be a frozen formulation, a lyophilized formulation, a spray-dried formulation, a spray-freeze-dried formulation, a supercritically dried formulation, an evaporated formulation, or a rotary evaporated formulation. In some embodiments, the solid state formulation is a frozen formulation or a lyophilized formulation. In some cases, the solid state formulation is a frozen formulation. In various cases, the solid state formulation is a lyophilized formulation. As used herein, "macromolecule" refers to a molecule containing a large number of atoms, such as 1000 or more atoms, and/or a molecule mass of at least about 1 dalton, and/or a diameter of about 100 or more angstroms. Examples of macromolecules include proteins, nucleic acids, polymers, and dendrimers. In some embodiments, the macromolecule of the disclosure is a biologic molecule. As used herein, "biologic molecule" refers to a molecule that is produced from living organisms or contains components of living organisms. Contemplated biologic molecules include, for example, proteins and nucleic acids. In some cases, the biologic is a protein. Contemplated proteins include antibodies and fusion proteins. As used herein, "fusion protein" refers to a protein including at least two domains that are encoded by separate genes that have been joined so that they are transcribed and translated as a single unit." In various cases, the antibody is a monoclonal antibody ("mAb"). In some cases, the fusion protein is a bispecific antibody construct. As used herein "bispecific antibody construct" refers to a molecule that is formed from linking the targeting regions of two different antibodies together. In some cases, the bispecific antibody construct is a half-life extended bispecific antibody construct. In some embodiments, the macromolecule is a bispecific antibody construct as disclosed in PCT publication nos. WO 2008/119567 or WO 2017/134140, each of which are incorporated herein by reference in its entirety.

The solid state formulation can include one or more excipients. As used herein, "excipient" refers to a component of the solid state formulation other than water and the macromolecule. Suitable excipients include, but are not limited to, buffers; stabilizers, such as such as amino acids and amino acid derivatives, polyethylene glycols and polyethylene glycol derivatives, polyols, acids, amines, polysaccharides or polysaccharide derivatives, salts, and surfactants; pH adjusting agents; antioxidants; and cryoprotectants.

In some embodiments, the solid state formulation is a lyophilized formulation. A "lyophilized formulation" refers to a formulation that has been freeze-dried. In various embodiments, the lowest temperature at which the $T_1$ experiment is conducted on a lyophilized formulation is in a range from about −100° C. to about 25° C., or about −100° C. to about −10° C., or about −50° C. to about −30° C., and the highest temperature at which the $T_1$ experiment is conducted on a lyophilized formulation is in a range from about 50° C. to about 150° C., or about 75° C. to about 150° C., or about 100° C. to about 150° C. In some cases, the highest and lowest temperatures have a difference of at least about 50° C., or at least about 75° C., or at least about 100° C. In some embodiments, the $T_1$ experiment on a lyophilized formulation is conducted at every 10 degrees, or every 9 degrees, or every 8 degrees, or every 7 degrees, or every 6 degrees, or every 5 degrees, or every 4 degrees, or every 2 degrees, or every 1 degree Celsius in the temperature range. In some cases, the $T_1$ experiment is conducted at every 3 degrees Celsius in the temperature range. In some embodiments, the $T_1$ experiment on a lyophilized formulation comprises a variable delay period in a range from about 0.01 seconds to about 60 seconds. In some cases, the $T_1$ value for a lyophilized formulation at each temperature is generated using monoexponential curve fitting. In various embodiments, the $T_1$ experiment comprises three variable delay times at each temperature to generate three FID plots at each temperature. In some embodiments, the $T_1$ experiment comprises four variable delay times at each temperature to generate four FID plots at each temperature. In some cases, the $T_1$ experiment comprises five variable delay times at each temperature to generate five FID plots at each temperature.

In some cases, the $T_1$ experiment comprises six variable delay times at each temperature to generate six FID plots at each temperature.

In some embodiments, the solid state formulation is a lyophilized formulation and: the saturation recovery curve is generated by plotting the signal intensity of each of the at least three FID plots versus delay time; the $T_1$ experiment comprises baseline suppression and magic angle spinning; steps (d)-(f) are repeated at 15 or more temperatures; each temperature is in a range from about −50° C. to about 150° C.; the highest and lowest temperatures have a difference from about 75° C. to about 100° C.; in each equilibrating step the solid state formulation is held at the temperature for a duration in the range of about one minute to about ten minutes before conducting the $T_1$ experiment; the method excludes retuning and recalibrating the ssNMR probe after equilibrating at the first temperature; the variable delay period is in a range from about 0.01 seconds to about 60 seconds; and each $T_1$ experiment comprises six variable delay times at each temperature to generate six FID plots at each temperature.

In various embodiments, the solid state formulation is a frozen formulation. As used herein, a "frozen formulation" is a formulation at a temperature below the melting point of the formulation. The lowest temperature at which the $T_1$ experiment is conducted on a frozen formulation is a temperature below the $T_g$ of the solid state formulation. In various embodiments, the lowest temperature at which the $T_1$ experiment is conducted is in a range from about −100° C. to about 0° C., or about −100° C. to about −10° C., or about −50° C. to about −30° C., and the highest temperature at which the $T_1$ experiment is conducted on a frozen formulation is in a range from about −15° C. to about 0° C., or about −15° C. to about −10° C., or about −10° C. to about 0° C. In some cases, the highest and lowest temperatures have a difference of at least about 30° C., or at least about 45° C., or at least about 50° C. In some embodiments, the $T_1$ experiment is conducted on a frozen formulation at every 10 degrees, or every 9 degrees, or every 8 degrees, or every 7 degrees, or every 6 degrees, or every 5 degrees, or every 4 degrees, or every 2 degrees, or every 1 degree Celsius within the temperature range. In some cases, the $T_1$ experiment is conducted at every 2 degrees Celsius within the temperature range. In some embodiments, the $T_1$ experiment is comprises a variable delay period in a range from about 0.01 seconds to about 240 seconds. In some cases, the $T_1$ value at each temperature for a frozen formulation is generated using biexponential curve fitting. As described above, a frozen formulation includes both ice and freeze concentrate (which is everything except the ice), each of which has a separate relaxation time, which can be extracted in a single biexponential fit. In various embodiments, the $T_1$ experiment comprises five variable delay times at each temperature to generate five FID plots at each temperature. In some embodiments, the $T_1$ experiment comprises six variable delay times at each temperature to generate six FID plots at each temperature. In some cases, the $T_1$ experiment comprises seven variable delay times at each temperature to generate seven FID plots at each temperature. In some cases, the $T_1$ experiment comprises eight variable delay times at each temperature to generate eight FID plots at each temperature. In some embodiments, the $T_1$ experiment comprises nine variable delay times at each temperature to generate nine FID plots at each temperature.

In some embodiments, the solid state formulation is a frozen formulation and: the saturation recovery curve is generated by plotting the signal intensity of each of the at least three FID plots versus delay time; the $T_1$ experiment comprises baseline suppression and magic angle spinning; steps (d)-(f) are repeated at 25 or more temperatures; each temperature is in a range from about −50° C. to about 0° C.; the highest and lowest temperatures have a difference from about 25° C. to about 40° C.; in each equilibrating step the solid state formulation is held at the temperature for a duration in the range of about one minute to about ten minutes before conducting the $T_1$ experiment; the method excludes retuning and recalibrating the ssNMR probe after equilibrating at the first temperature; the variable delay period is in a range from about 0.01 seconds to about 240 seconds; and each $T_1$ experiment comprises nine variable delay times at each temperature to generate nine FID plots at each temperature.

In some embodiments, the saturation recovery curve is analyzed to determine the ratio of the ice and the freeze concentrate. Such an analysis advantageously provides a phase map of the frozen formulation and allows the quantification of ice present in the formulation.

Relaxation Rate Curve

In some embodiments, the methods disclosed herein can further include the steps: (g) converting each $T_1$ value to $^1H$ spin-lattice relaxation rate ("$R_1$"), and (h) plotting $R_1$ versus temperature to generate a relaxation rate curve for the solid state formulation. The $T_1$ at each temperature can be converted to relaxation rate $R_1$ using the equation $R_1=1/T_1$. The methods disclosed herein also can further comprise analyzing the relaxation rate curve to determine the molecular mobility of the macromolecule in the solid state formulation, the degree of aggregation in the solid state formulation, and/or the stability of the solid state formulation.

Figure 6:
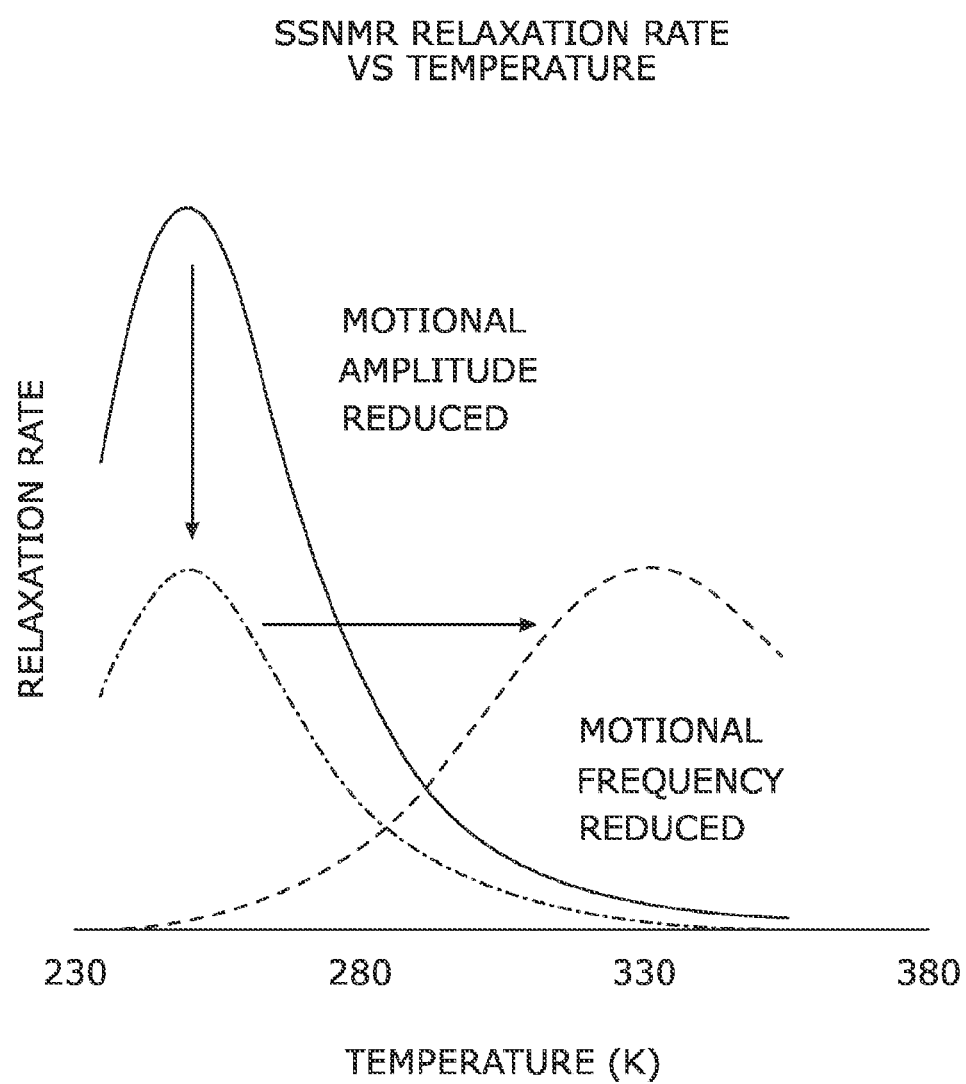
FIG. 6 is a diagram depicting the effects of reducing the motional amplitude and frequency on the $R_1$ vs temperature curve for a given idealized motional mode.

The relaxation rate curve in ssNMR is a sum of all molecular motions and provides information about the molecular motion of a macromolecule, such as a biologic molecule, in a solid state formulation, and thus, the stability of the solid state formulation. For example, increased stability of a solid state formulation can be indicated by, for example, reduced amplitude of motion, reduced frequency of motion, and/or increased activation energy of motion. FIG. 6, for example, shows theoretical ssNMR relaxation rate curves and demonstrates that a longer relaxation time (or slower relaxation rate) results in a relaxation rate curve having a lower maximum peak value, or reduced motional amplitude, correlating to a lesser degree of molecular motion, and thus, a lesser amount of aggregation, which is indicative of a more stable formulation. In contrast, a shorter relaxation time (or faster relaxation rate) results in a relaxation rate curve having a higher maximum peak value, or increased motional amplitude, which indicates that the solid state formulation exhibits a greater degree of molecular motion, and thus a greater degree of aggregation. As such, the solid state formulation is less stable. In other words, the higher the R1 value, the higher the aggregation rate. FIG. 6 further demonstrates that a shift in the maximum peak to a higher temperature correlates to reduced motional frequency, which relates to a more stable formulation. Further, a narrower relaxation peak is indicative of an increase in the activation energy of motion. In some cases and without intending to be bound by any particular theory, when comparing the relaxation curves of multiple formulations, the increase in stability is greatest for an increase in the temperature of maximum $R_1$, followed by a narrowing of the relaxation peak, followed by a reduction in the $R_1$ curve amplitude.

Figures 7A, 7B, 7C:
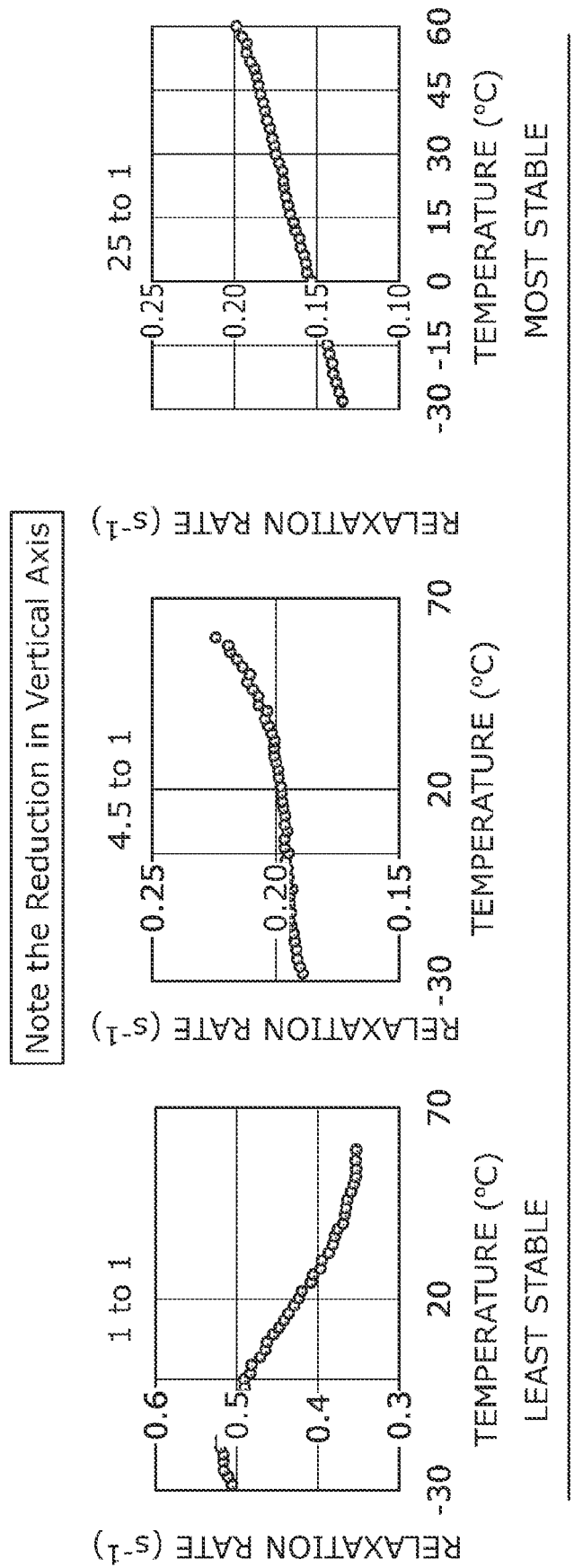
FIG. 7A is a $R_1$ vs temperature curve for 1:1 lyophilized trehalose:anti-streptavidin.
FIG. 7B is a $R_1$ vs temperature curve for 4.5:1 lyophilized trehalose:anti-streptavidin.
FIG. 7C is a $R_1$ vs temperature curve for 25:1 lyophilized trehalose:anti-streptavidin.
Figure 8:
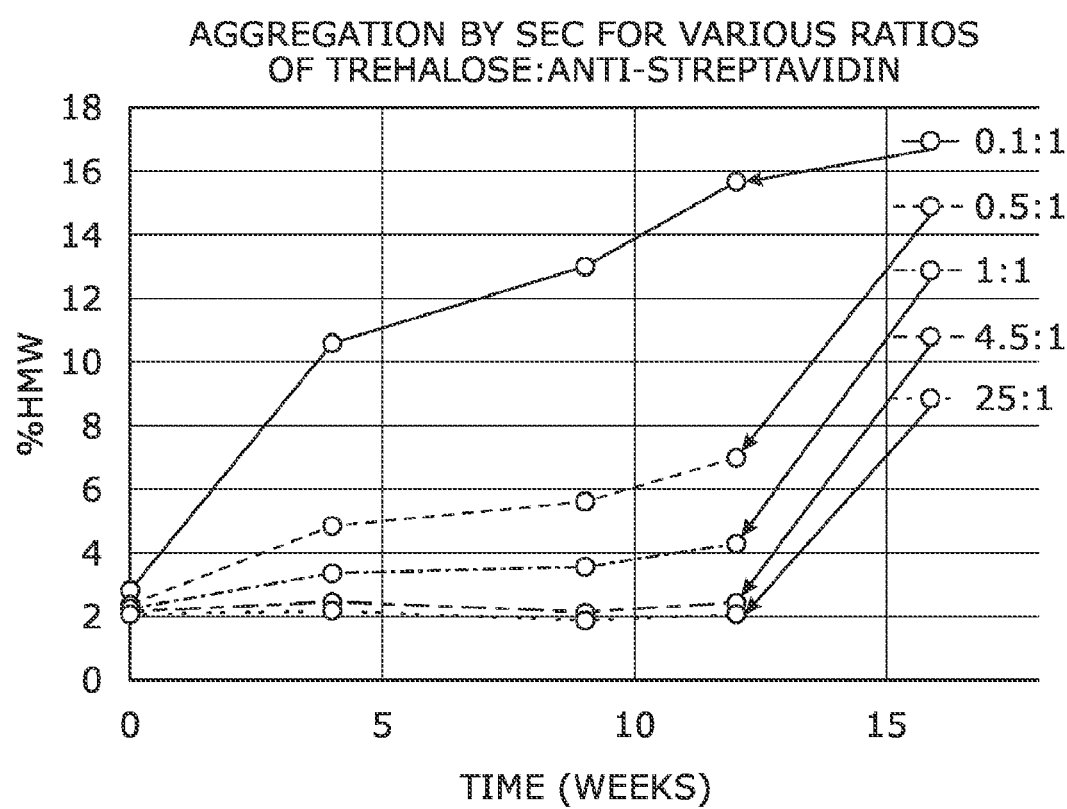
FIG. 8 shows aggregation of different ratios of lyophilized trehalose:anti-streptavidin formulations detected by size-exclusion chromatography (SEC), demonstrating that increasing trehalose correlates to decreasing aggregation.
Figure 9:
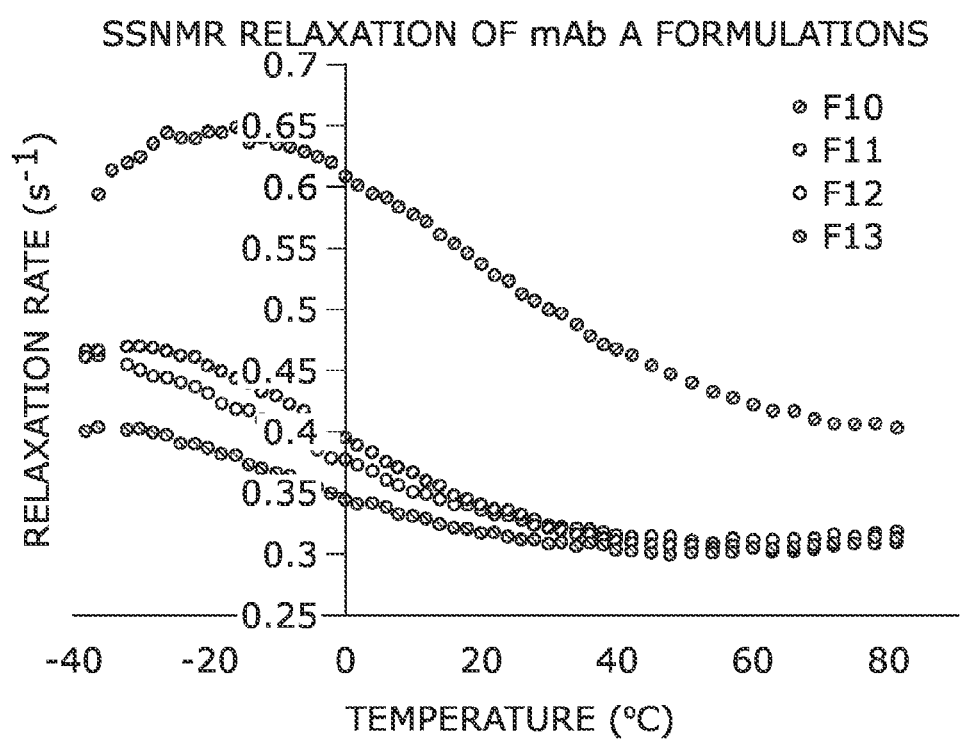
FIG. 9 shows $R_1$ relaxation vs temperature curves for formulations of mAb A with varying trehalose to protein ratios of 0.7 (F10), 0.9 (F11), 0.9 (F12), and 1.1 (F13), demonstrating that the trend in aggregation under accelerated conditions (40° C.) is F10>F11>F12>F13, with F13 being the most stable formulation.

The methods disclosed herein are reliable for determining formulation stability because they provide results that are consistent with the results generated from methods traditionally used for determining the stability of macromolecule-containing formulations. For example, when lyophilized formulations containing different ratios and concentrations of trehalose and protein were subjected to: (1) the ssNMR methods described herein, (2) traditional solution techniques for determining protein stability, and (3) traditional solution techniques for determining protein stability under accelerated conditions, the methods described herein produced stability results that were consistent with the results produced using the traditional methods. See Examples 2 and 3 and FIGS. 7-9. For example, and as shown in FIGS. 7 and 9, the ssNMR method disclosed herein demonstrates that as the relative amount of sugar (trehalose) is increased aggregation decreases, which is indicated by the formulation shifting to a lower mobility state with increasing amounts of sugar (e.g., the maximum $R_1$ value decreases and the temperature at which the maximum $R_1$ value occurs increases). As shown in FIG. 8, the same aggregation trend (aggregation decreases with increased sugar concentration) was demonstrated using the traditional solution techniques.

The methods disclosed herein can be used to assess the effect of factors that can cause instability in a solid state formulation, such as moisture content, compound structure (e.g., presence or absence of an intra-domain disulfide bridge), compound size, presence/absence of excipients), and/or process conditions (e.g., freezing rate) on molecular motion, compound aggregation, and/or solid state formulation stability.

Figure 10:
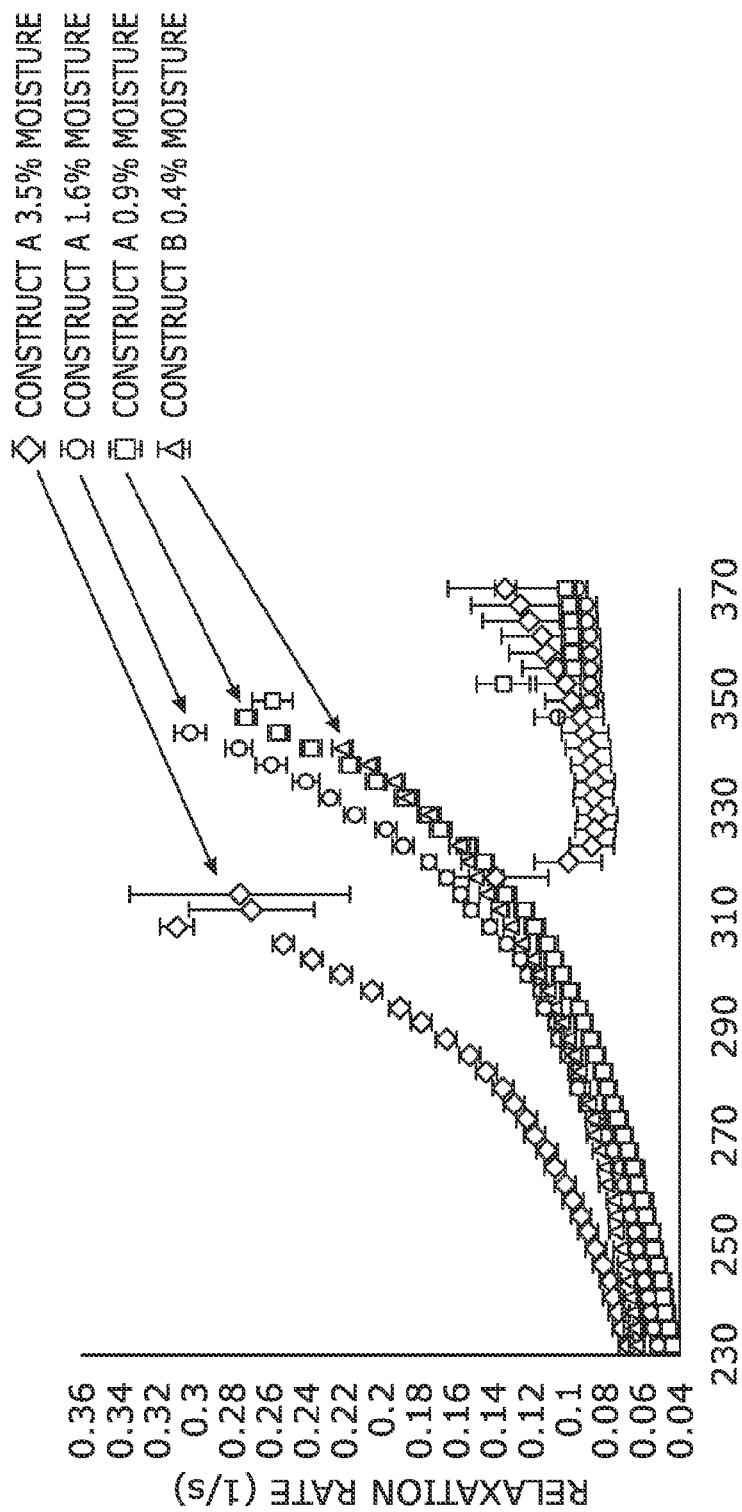
FIG. 10 shows $R_1$ relaxation vs temperature curves for Construct A and Construct B lyophilized drug products at various moisture levels, demonstrating the effect of increasing moisture on molecular mobility, which shifts the relaxation peak to lower temperatures indicating faster molecular motions.
Figure 11:
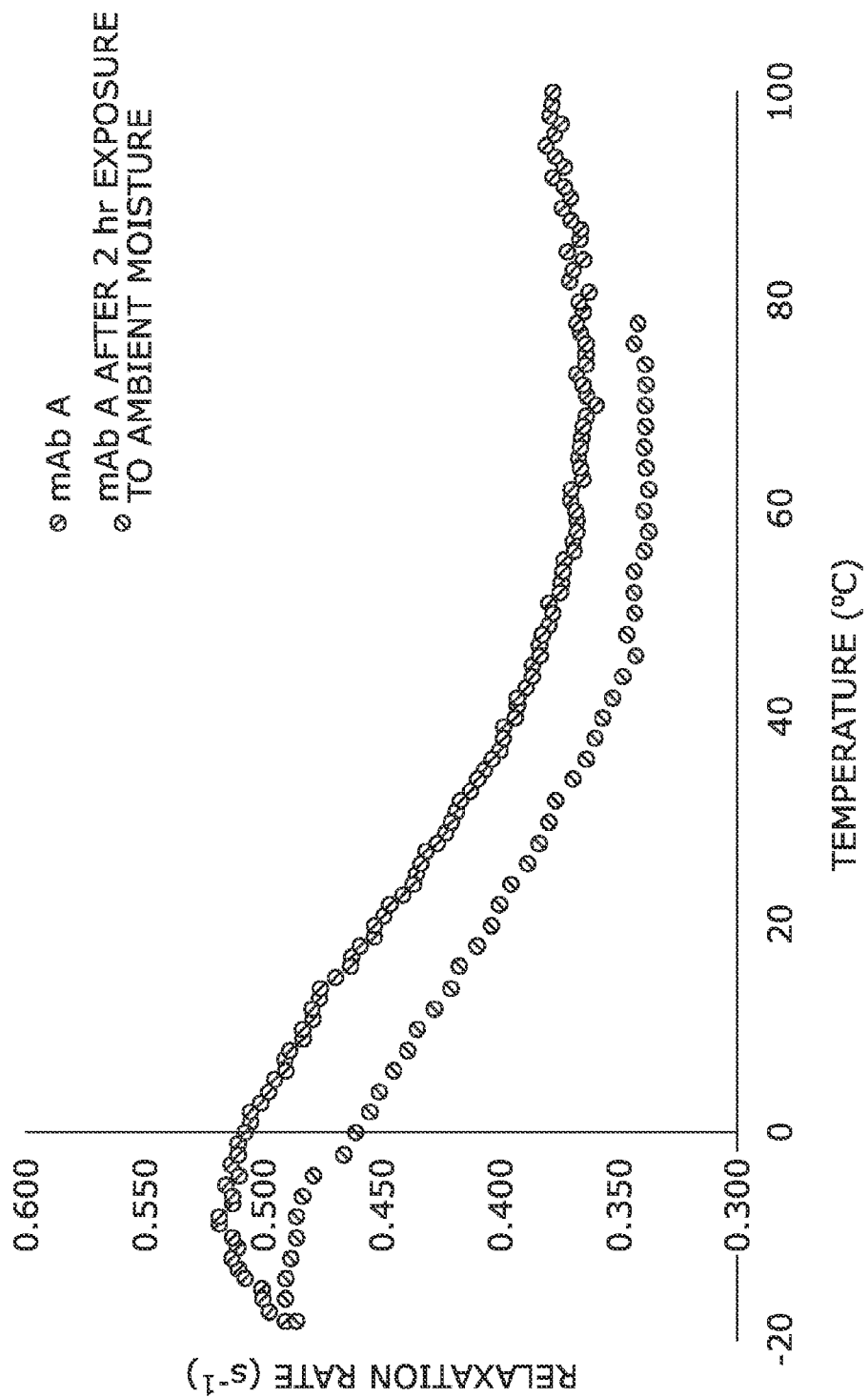
FIG. 11 shows the relaxation vs temperature curve for mAb A and mAb A exposed to water $H_2O$ for two hours. This shows that moisture levels can impact the relaxation properties of the formulations and impact stability.

The methods described can provide information about the amount of moisture in a solid state sample, as well as the temperature at which a formulation including residual moisture is resistant to aggregation (e.g., remains stable). Without intending to be bound by any particular theory, increased moisture in a sample results in increased molecular mobility and decreased stability. See, e.g., Example 4, FIG. 10. As shown in FIG. 10, as the amount of residual moisture in the formulation increased, the $R_1$ value increased, indicating a less stable formulation. The amount of moisture content in a formulation coupled with the temperature of the formulation can dictate whether the formulation is in a high mobility state or a low mobility state. The formulation does not generally exhibit a continuous spectrum of mobility with increasing temperature. The curves of FIG. 10 show the temperatures at which the test formulation remains in a low mobility state, i.e., the temperatures at which $R_1$ remains low, rather than an undesired high mobility state. For the formulations described in Example 4 that have 1.5% or less residual moisture, relatively low mobility was demonstrated at temperatures of about 290K or less, with a transition to a high mobility state at temperatures above 290K. In contrast, for the formulations of Example 4 having a 3% residual moisture content, the low mobility state was present only for temperatures of about 230K or less, with the transition to high mobility state occurring at temperatures above about 230K. See also FIG. 11, which shows comparison relaxation versus temperature curves for a protein that has and has not been exposed to atmospheric moisture for two hours.

The methods disclosed herein also can be used to determine the effect of macromolecule composition (e.g., number of intra-domain disulfide bridges) or macromolecule size on the stability of a macromolecule-containing solid state formulation. For example, the methods described herein demonstrated that an additional intra-domain disulfide bridge on a bispecific antibody construct resulted in decreased molecule motion, and thus, a more stable solid state formulation. As such, the methods described herein advantageously allow the identification of protein domains that are responsible for motion and aggregation. See Example 5, FIG. 12. The methods described herein also allow the determination of how the size of the macromolecule can effect motion in the solid state leading to changes in aggregation. As shown in Example 7, FIG. 16, a smaller antibody construct exhibited more motion in the solid state, and thus less stability, than a larger antibody construct.

The methods described herein also can be used to determine the effect of an excipient (e.g., citrate or benzyl alcohol) on the stability of a macromolecule-containing solid state formulation. For example, the methods disclosed herein show that the presence of benzyl alcohol in the tested formulations reduced aggregation in all bispecific antibody constructs, resulting in more stable formulations, the exception being Construct C, which had too much innate molecular motion to overcome due to lack of an intra-domain disulfide bridge. In contrast, the inclusion of citrate as an excipient in the tested formulations had no effect on construct mobility, and thus, formulation stability. See Example 6 and FIGS. 13-15.

Figure 17:
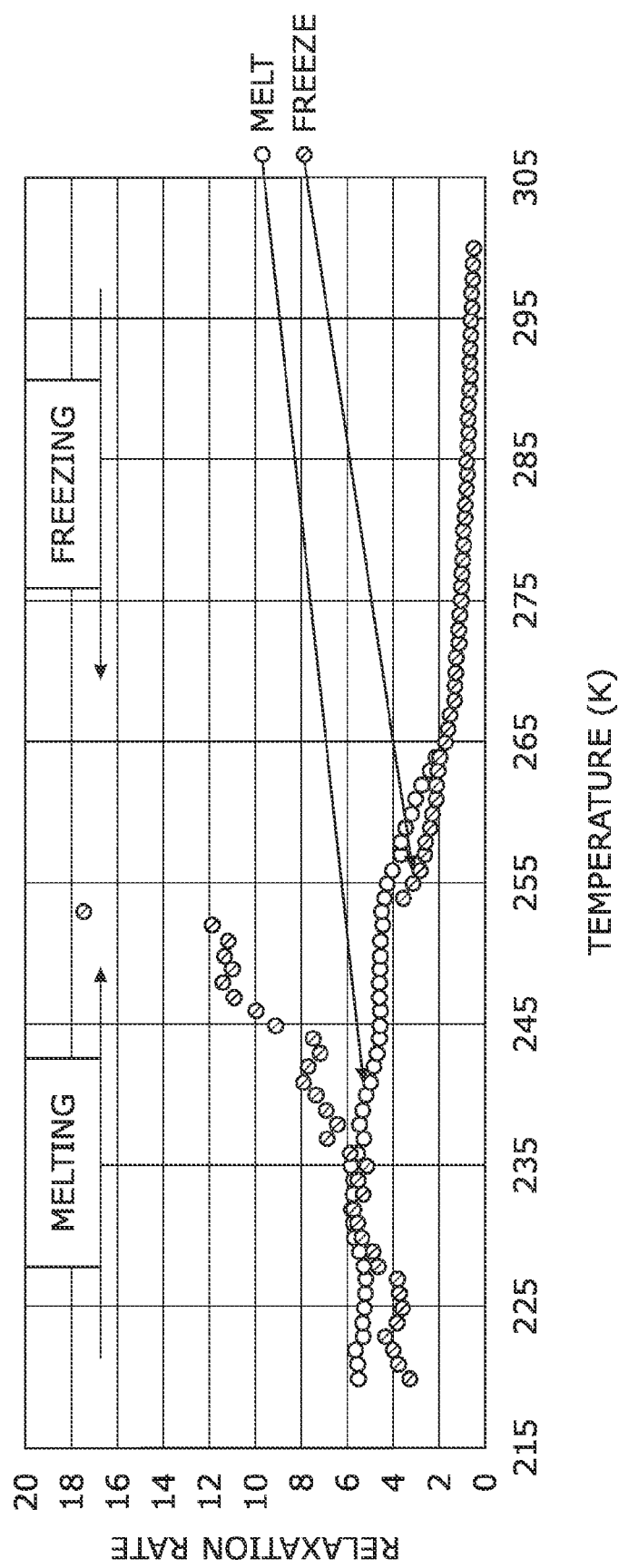
FIG. 17 shows the relaxation rate vs temperature curves for non-ice material of freezing vs melting of a formulation including Construct E. These curves show that the freezing rate can impact the relaxation curves, thus making the measurements sensitive to freezing process parameters.
Figure 18:
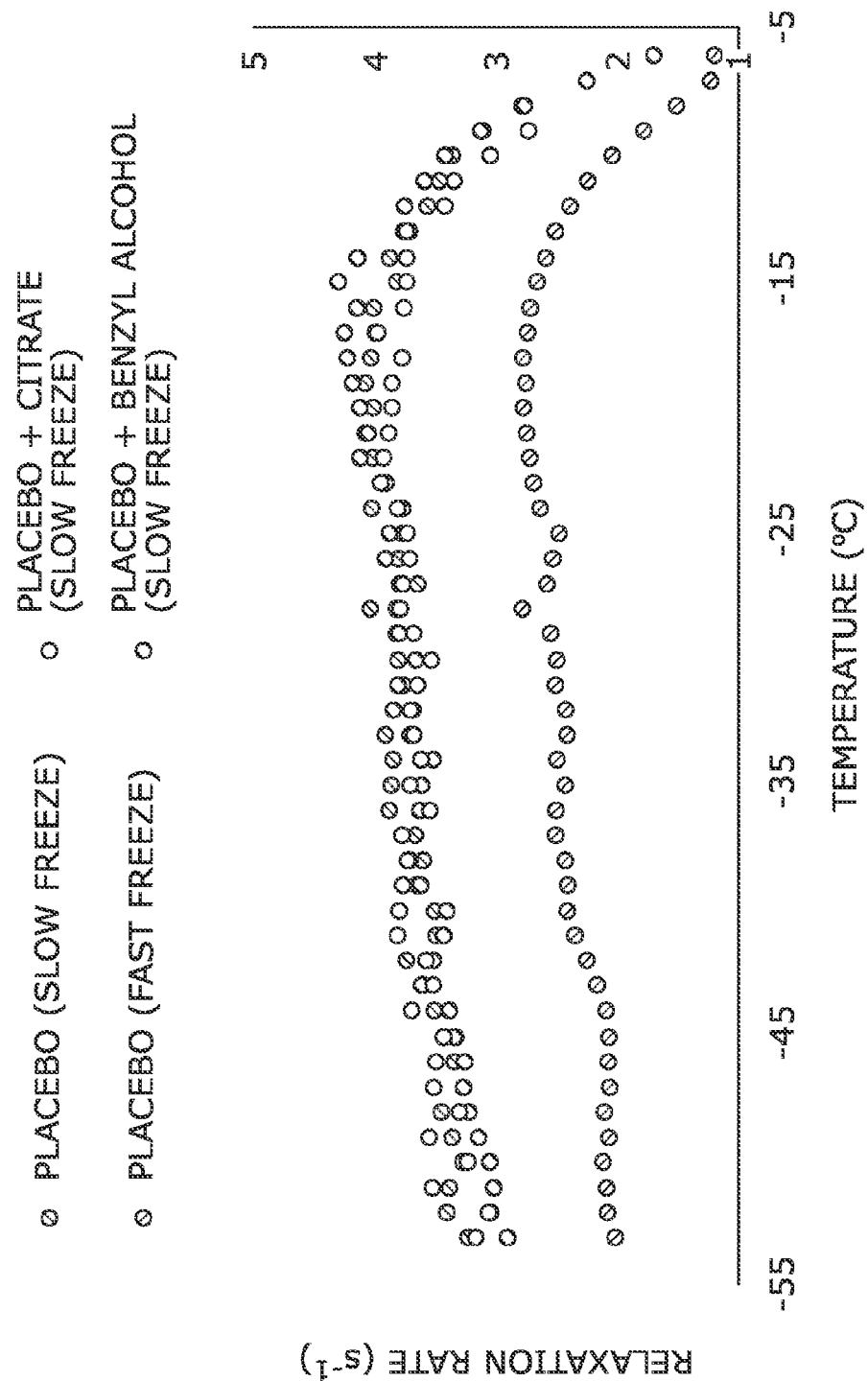
FIG. 18 shows the relaxation rate vs temperature curves for a fast freezing process (greater than 5° C./minute) versus a slow freezing process (1° C./minute) for placebo formulations. The data show that the methods described herein can detect changes in the frozen state due to changes in freezing conditions.

The methods described herein also can be used to determine the effect of process conditions on the stability of a macromolecule-containing solid state formulation. As shown in FIG. 17 and FIG. 18, the methods described herein provide information on the effect of freezing rate on frozen solid state formulation, demonstrating that the stability of a frozen formulation is greater if it had been subjected to fast freezing rather than slow freeze.

Thus, the methods described herein provide valuable information regarding formulation stability at an early stage in the formulation process, allowing one to determine which factors adversely affect or beneficially improve formulation stability. Such knowledge allows early identification of the most promising macromolecule-containing solid state formulation among a group of test macromolecule-containing solid state formulations and reformulation of a solid state formulation, accelerating formulation development.

As such, provided herein is a method of selecting a macromolecule-containing solid state formulation among a group of test macromolecule-containing solid state formulations, the method comprising: (I) generating a relaxation rate curve for each macromolecule-containing solid state formulation in the group of test macromolecule-containing solid state formulations; wherein the relaxation rate curve is generated by the method previous described herein (e.g., determining $T_1$ of each formulation by conducting a $T_1$ experiment at three or more temperatures using saturation recovery having at least three variable delay times, and optionally, baseline suppression, to generate a FID plot at each temperature, generating a saturation recovery curve from each FID plot, fitting each saturation recovery curve to a nonlinear regression equation to generate a $T_1$ value at each temperature, taking the inverse of $T_1$ to determine $R_1$, and plotting $R_1$ versus temperature to generate the relaxation rate curve); (II) comparing the maximum $R_1$ peak value of each curve, the temperature of the maximum $R_1$ peak in each curve, the width of the maximum $R_1$ peak in each curve, or a combination thereof; and (III) selecting the solid state formulation which has the highest temperature of the maximum $R_1$ peak, or the narrowest $R_1$ peak width, or lowest maximum $R_1$ peak value. In some embodiments when one solid state formulation has the highest temperature of the maximum $R_1$ peak and another solid state formulation has the narrowest $R_1$ peak width, then the solid state formulation with the highest temperature of the maximum $R_1$ peak is selected. In some cases when one solid state formulation has the highest temperature of the maximum $R_1$ peak and another solid state formulation has the lowest maximum $R_1$ peak value, then the formulation with the highest temperature of the maximum $R_1$ peak is selected. In various cases when one of the solid state formulations has the narrowest $R_1$ peak width and another solid state formulation has the lowest maximum $R_1$ peak value, then the formulation with the narrowest $R_1$ peak width is selected. In some cases when one solid state formulation has the highest temperature of the maximum $R_1$ peak, a second solid state formulation has the narrowest $R_1$ peak width, and a third solid state formulation has the lowest maximum $R_1$ peak value, then the formulation with the highest temperature of the maximum $R_1$ peak is selected.

Also provided herein is a method of selecting a formulation excipient for use in a macromolecule-containing solid state formulation, the method comprising: (I) generating a relaxation rate curve for each macromolecule-containing solid state formulation in a group of test macromolecule-containing solid state formulations, each formulation having a different composition of excipients, a different amount of one or more excipients, or both; wherein the relaxation rate curve for each macromolecule-containing solid state formulation is generated by the method previous described herein (e.g., determining $T_1$ of each formulation by conducting a $T_1$ experiment at three or more temperatures using saturation recovery having at least three variable delay times, and optionally, baseline suppression, to generate a FID plot at each temperature, generating a saturation recovery curve from each FID plot, fitting each saturation recovery curve to a nonlinear regression equation to generate a $T_1$ value at each temperature, taking the inverse of $T_1$ to determine $R_1$, and plotting $R_1$ versus temperature to generate the relaxation rate curve); (II) comparing the maximum $R_1$ peak value of each curve, the temperature of the maximum $R_1$ peak of each curve, the width of the maximum $R_1$ peak of each curve, or a combination thereof; and (III) selecting an excipient that is present in the solid state formulation with the lowest maximum $R_1$ peak value, the highest temperature of the maximum $R_1$ peak, or the narrowest $R_1$ peak width. In some embodiments when one solid state formulation has the highest temperature of the maximum $R_1$ peak and another solid state formulation has the narrowest $R_1$ peak width, then the excipient is selected from the solid state formulation with the highest temperature of the maximum $R_1$ peak. In some cases when one solid state formulation has the highest temperature of the maximum $R_1$ peak and another solid state formulation has the lowest maximum $R_1$ peak value, then the excipient is selected from formulation with the highest temperature of the maximum $R_1$ peak. In various cases when one of the solid state formulations has the narrowest $R_1$ peak width and another solid state formulation has the lowest maximum $R_1$ peak value, then the excipient is selected from the formulation with the narrowest $R_1$ peak width. In some cases when one solid state formulation has the highest temperature of the maximum $R_1$ peak, a second solid state formulation has the narrowest $R_1$ peak width, and a third solid state formulation has the lowest maximum $R_1$ peak value, then the excipient is selected from the formulation with the highest temperature of the maximum $R_1$ peak is selected.

The following examples are provided for illustration and are not intended to limit the scope of the invention.

EXAMPLES

General Procedures

All NMR data was collected on a Bruker 500 MHz NMR Spectrometer or equivalent. The pulse sequence used for measuring $T_1$ was a standard saturation recovery sequence with a baseline suppression sequence (as disclosed in D. G. Cory & W. M. Ritchey, J. Magn. Reson. 80, 128-132 (1988)) before detection of the FID, as shown in FIG. 1. In particular, 2.5 μs π/2 pulses and 5 μs π pulses, a saturation loop consisting of 300 π pulses with 20 μs and 2 μs delays between the π/2-delay-π-delay-π baseline suppression were used. The NMR probe was calibrated to 2.5 π/2 pulses, tuned, and matched at room temperature prior to data collection. Retuning and recalibrating of the probe were not necessary to collect the relaxation data across the available temperature range of the probe. A 4.0 mm magic angle spinning ("MAS") probe, or equivalent, with a sample volume of approximately 804 was used. MAS frequencies ranged between 2.0 kHz and 16 kHz and were generally around 8.0 kHz.

In cases where variable delays were used in $T_1$ experiments, the following delays were used. For lyophilized samples: 0.01 s, 0.03 s, 0.1 s, 0.3 s, 1 s, 8 s, 12 s, and 60 s. For frozen samples: 0.01 s, 0.03 s, 0.1 s, 0.3 s, 0.5 s, 1 s, 3 s, 80 s, and 240 s.

$T_1$ vs temperature data was collected. The magnitude of the $1^{st}$ point of the FID (or max) was fit, I(t), to exponential to determine $T_1$. $R_1$ was determined by taking the inverse of $T_1$, and $R_1$ was plotted against temperature to provide a plot of the relaxation rate vs temperature. Data acquisition and processing was automated via script.

Shifting of $R_1$ vs temperature curves down and to the right indicate greater stability and less aggregation of the formulations.

Example 1

Determination of Detection Sequence for $T_1$ Measurement

Figure 2:
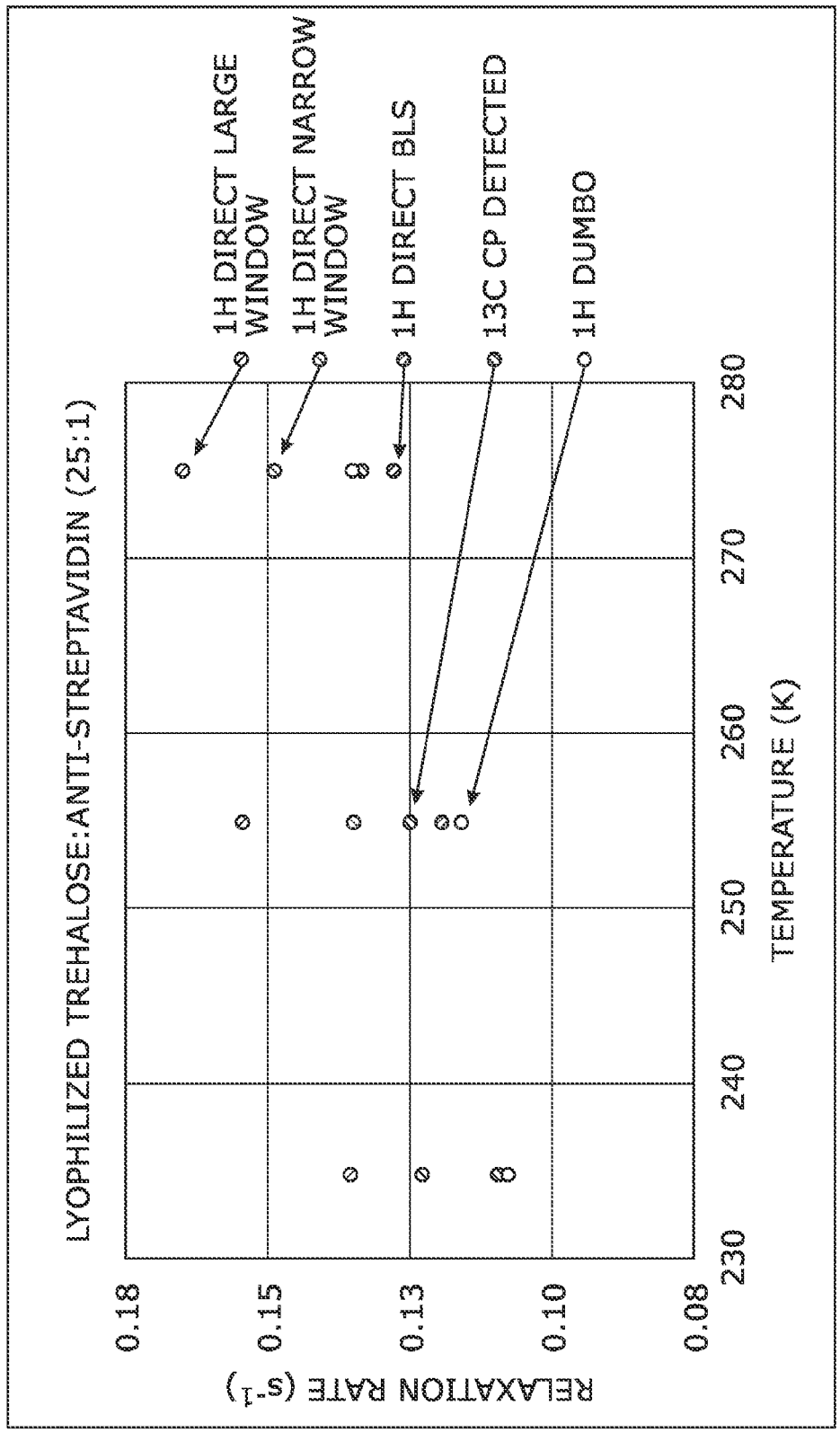
FIG. 2 shows a comparison of $^1$H $R_1$ relaxation rates measured using a saturation recovery sequence combined with various detection methods for lyophilized 25:1 trehalose: anti-streptavidin. "BLS" stands for baseline suppression.
Figure 3:
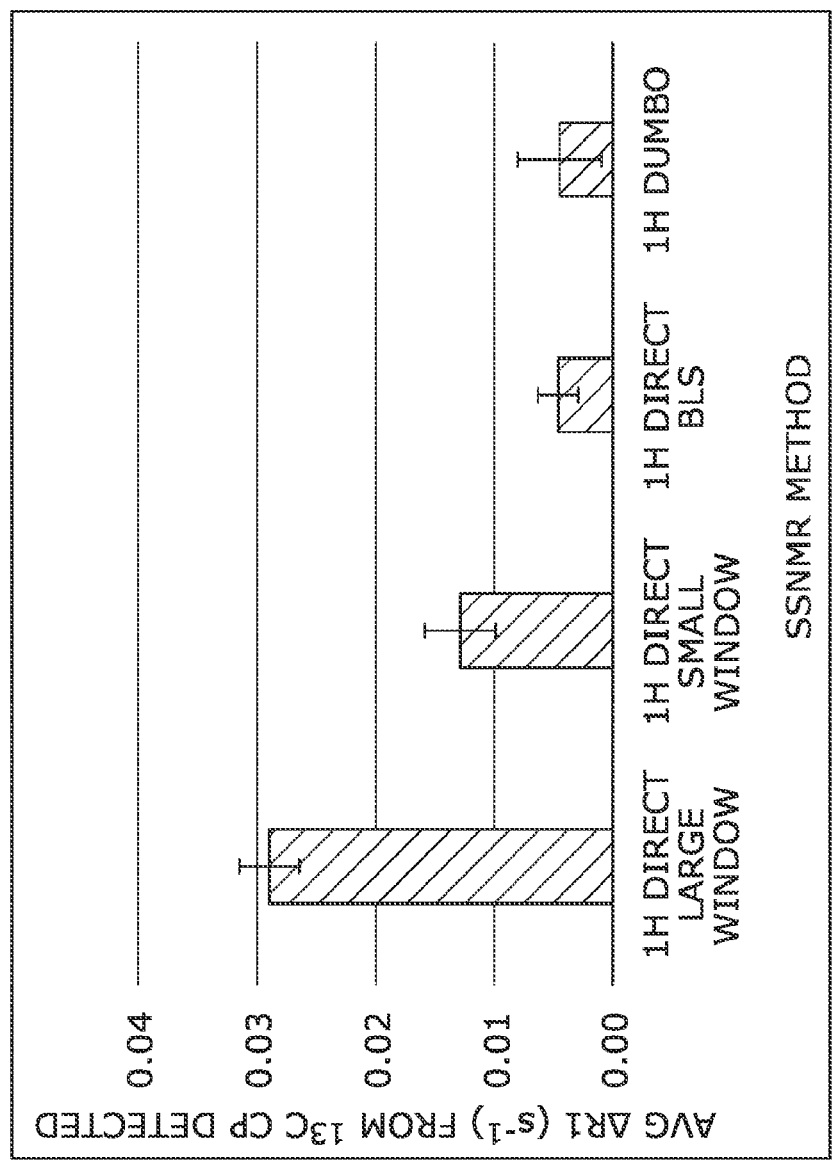
FIG. 3 shows the average difference from $^{13}$C cross-polarization detected $^1$H $R_1$ relaxation rate for $^1$H relaxation rates measured using a saturation recovery sequence combined with various detection methods for lyophilized 25:1 trehalose:anti-streptavidin.
Figure 4:
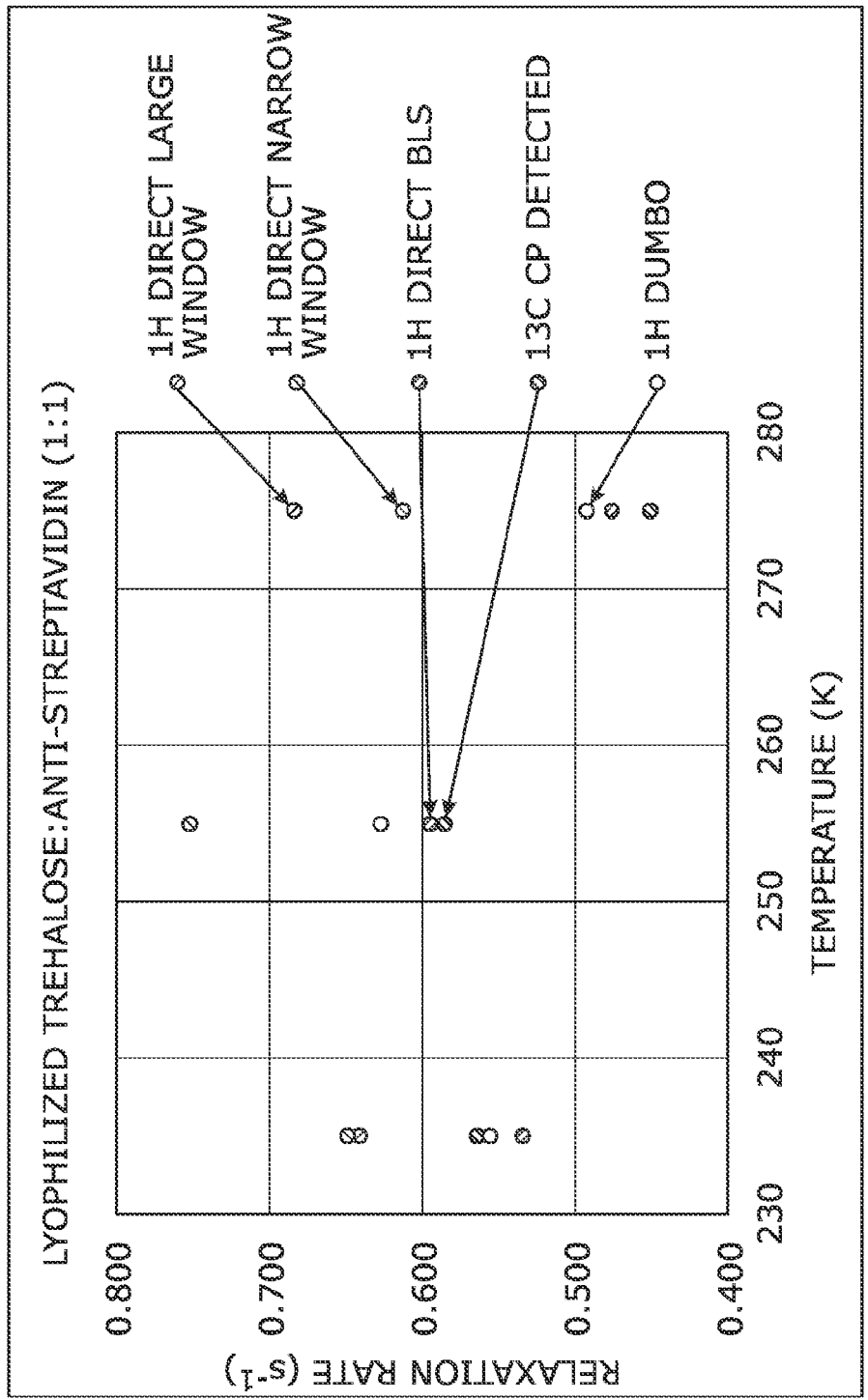
FIG. 4 shows a comparison of $^1$H $R_1$ relaxation rates measured using a saturation recovery sequence combined with various detection methods for lyophilized 1:1 trehalose: anti-streptavidin.
Figure 5:
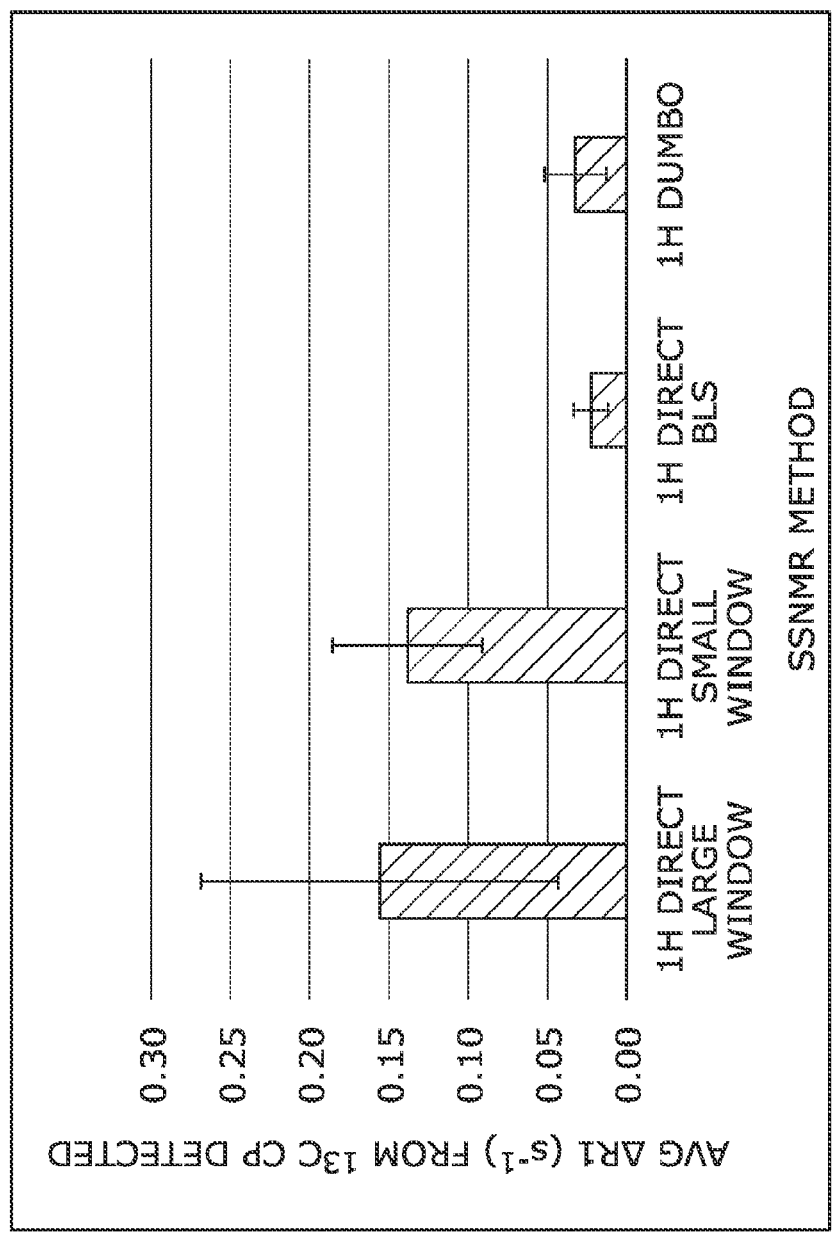
FIG. 5 shows the average difference from $^{13}$C CP detected $^1$H $R_1$ relaxation rate for $^1$H relaxation rates measured using a saturation recovery sequence combined with various detection methods for lyophilized 1:1 trehalose:anti-streptavidin.

Five ssNMR detection schemes were considered for determination of $T_1$: $^1$H Direct Large Window, $^1$H Direct Narrow Window, $^1$H Direct Base Line Suppression, $^{13}$C cross polarization ("CP") Detected, $^1$H Dumbo. $T_1$ times for samples of lyophilized 25:1 and 1:1 trehalose:anti-streptavidin at 235K, 255K, and 275K were collected using each detection sequence and the $R_1$ for each determined. FIG. 2 shows a plot of the relaxation rate vs temperature for the 25:1 trehalose: anti-streptavidin samples for each of the detection methods, and FIG. 3 shows the corresponding change in $R_1$ for each detection sequence, relative to the $^{13}$C CP Detected method, the traditional NMR method for determining the mobility of macromolecules in the solid state. FIG. 4 shows a plot of the relaxation rate vs temperature for the 1:1 trehalose: anti-streptavidin samples for each of the detection methods, and FIG. 5 shows the corresponding change in $R_1$ for each detection sequence, relative to the $^{13}$C CP Detected method. As can be seen from the data in FIG. 2-FIG. 5, the $^1$H Direct Base Line Suppression detection sequence provided relaxation rates that were closest to the $^{13}$C CP Detected standard method. In addition, the $^1$H Direct Base Line Suppression detection sequence proved more robust to detuning and/or mis-calibration than the $^1$H Dumbo. Accordingly, the $^1$H Direct Base Line Suppression detection sequence was selected for data collection.

Example 2

Determination of Formulation Stability by ssNMR

Three lyophilized trehalose:anti-streptavidin samples were prepared and $T_1$ vs temperature was collected. The three samples had trehalose:anti-streptavidin ratios of 1:1, 4.5:1, and 25:1, respectively. Data were collected over a temperature range of about −30° C. to 60° C. The data were fit and the $R_1$ vs temperature plots prepared for each sample. FIG. 7 shows the $R_1$ vs temperature plots. As shown in FIG. 7A, the 1:1 sample was the least stable, having the highest peak relaxation rate, at the lowest temperature. As shown in FIGS. 7B and 7C, as the amount of sugar increases, the relaxation rate at low temperatures decreases, indicating a stabilization of the formulation at low temperatures.

The stability of lyophilized samples of trehalose:anti-streptavidin formulations having 0.1:1, 0.5:1, 1:1, 4.5:1, and 25:1 were also determined using the known solution state method, e.g., by size exclusion chromatography (SEC). The aggregation data for the formulations according to SEC is shown in FIG. 8. As shown in FIG. 8, the traditional solution state method also showed that increasing trehalose concentration results in decreased aggregation.

Thus, Example 2 demonstrates that the $^1$H ssNMR methods disclosed herein can be used to determine formulation aggregation and stability at least as well as the current solution state test methods.

Example 3

Effect of Protein Concentration on Stabilization

The effect of protein concentration on formulations including trehalose and protein was determined for 4 separate samples. Samples were prepared with the amount of trehalose and protein (monoclonal antibody A, "mAb A") as shown in the following table:

|     | TREHALOSE MG/ML | PROTEIN (mAb A) MG/ML | TREHALOSE TO PROTEIN RATIO |
| --- | --- | --- | --- |
| F10 | 17.0 | 23.1 | 0.7 |
| F11 | 20.8 | 23.1 | 0.9 |
| F12 | 17.0 | 18.9 | 0.9 |
| F13 | 20.8 | 18.9 | 1.1 |

$T_1$ vs temperature data was collected for each sample over a temperature range of about −40° C. to about 80° C. The $R_1$ vs temperature data was plotted and is shown in FIG. 9. As shown in FIG. 9, the trend in mobility and $R_1$ relaxation, which correlates to aggregation, is F10>F11>F12>F13. The trend shown in FIG. 9 is consistent with the trend in aggregation under accelerated conditions (40° C.) for the same formulations, with F13 being the most stable formulation.

Thus, Example 3 shows that the ssNMR method disclosed herein predicts trends in aggregation at least as well as known accelerated testing conditions.

Example 4

Effect of Moisture on Molecular Mobility

The effect of moisture on molecular mobility was determined as follows. Samples were prepared having a constant protein (bispecific antibody construct) concentration and variable moisture content. The amount of moisture in the samples is provided in the below table:

| Sample ID | Moisture content (by wt. of formulation) |
| --- | --- |
| Construct B | 0.4% |
| Construct A | 0.9% |
| Construct A | 1.6% |
| Construct A | 3.5% |

$T_1$ vs temperature data were collected for each sample over a temperature range of about −40° C. to about 95° C. The $R_1$ vs temperature data were plotted and is shown in FIG. 10. The effect of increasing moisture on molecular mobility is clearly shown for the 3% moisture sample, which has the relaxation peak shifted to lower temperatures indicating faster molecular motions in the range of about 5° C. to 25° C.

Thus, Example 4 shows that as the moisture in the sample is increased, molecular mobility increases, $R_1$ relaxation times decrease, and the stability of the formulation is expected to decrease (and aggregation increase).

Example 5

Determination of Differences in Molecular Mobility Between Placebo and Bispecific Antibody Construct Formulations and Between Bispecific Antibody Constructs Differences in molecular mobility between frozen bispecific antibody construct formulations and placebos can be demonstrated using the ssNMR methods of the disclosure. Two frozen bispecific antibody constructs with different aggregation behavior were tested as 1 mg/mL formulations. Construct D has an additional intra-domain disulfide bridge over Construct E. The placebo formulation tested included the same formulation as the construct formulations minus the construct itself.

Figure 12:
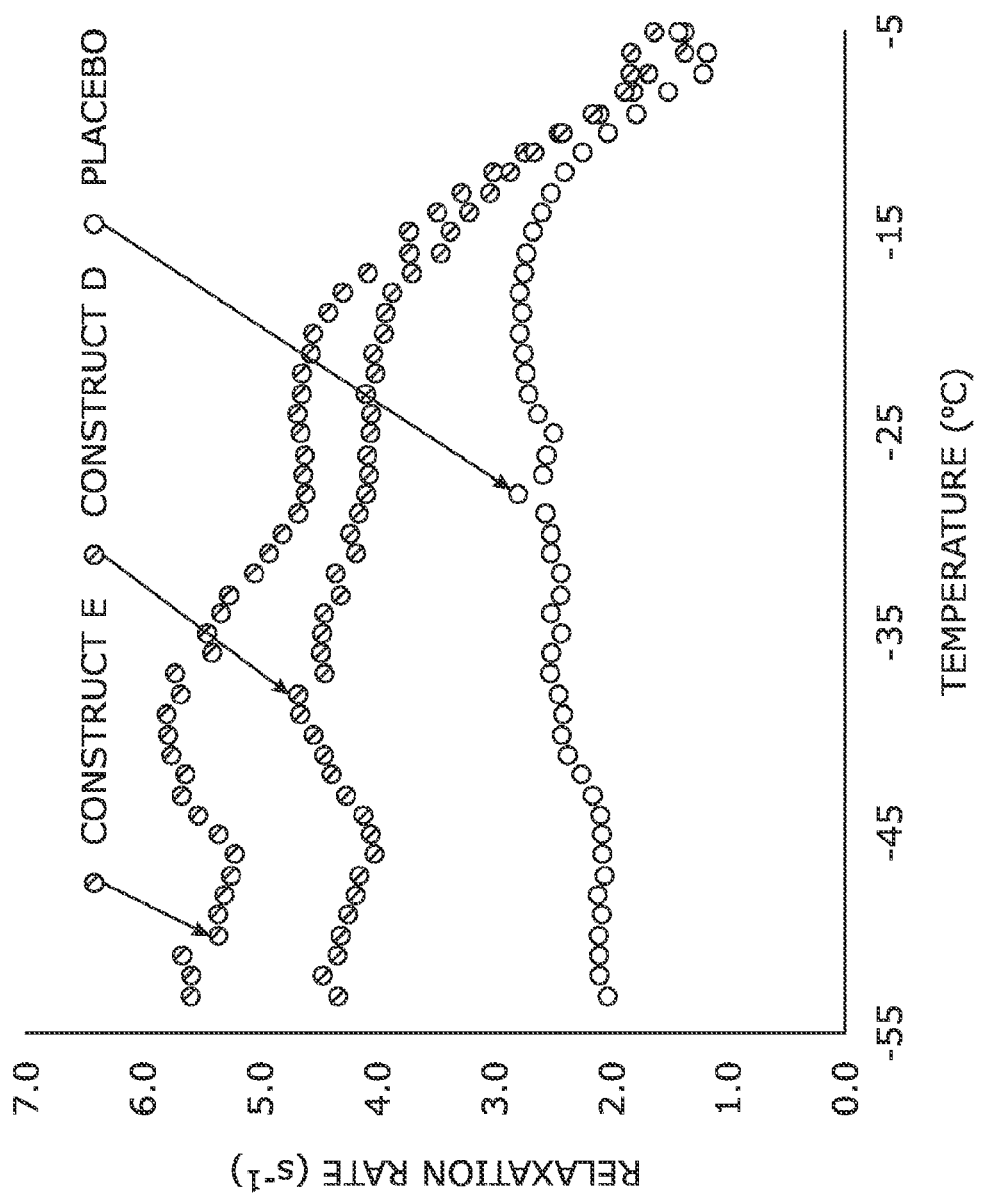
FIG. 12 shows the $R_1$ relaxation vs temperature curves for the non-ice, fast relaxing components of frozen formulations of a placebo with two different bispecific antibody constructs (Construct D and Construct E) at 1 mg/mL. Even at low concentrations the bispecific antibody constructs add a detectable increase in molecular mobility. Furthermore the reduction in mobility by adding an additional intra-domain disulfide bridge in one of the constructs can be seen in the reduction in the curves between the Construct E and Construct D constructs.

The samples were fast frozen to −53° C., and the $T_1$ measured as the temperature was increased. $R_1$ relaxation vs temperature for the non-ice, fast relaxing components of the frozen formulations of the placebo and two bispecific antibody constructs are shown in FIG. 12. Even at low concentrations, the bispecific antibody constructs add a detectable increase in molecular mobility. Further, the reduction in the mobility by adding an additional intra-domain disulfide bridge on the target binding domain can be seen in the reduction in the curves between Construct E and Construct D. Due to the reduction in mobility of Construct D, Construct D also had less aggregation than Construct E. This result is consistent with previous SEC data and literature on aggregation in lyophilized formulations.

Thus, Example 5 demonstrates that methods described herein can show how the addition of an intra-domain disulfide bridges to various domains of the bispecific antibody constructs (e.g., binding domain or Fc region) can lead to increased/decreased motion, decreased/increased aggregation, and decreased/increased stability in the solid state (e.g., frozen state), allowing the identification of domains that are responsible for motion and aggregation.

Example 6

Effect of Excipients on Molecular Motion

The effect of excipients on bispecific antibody construct aggregation and ssNMR relaxation was determined as follows. 500 μL samples were prepared from two different bispecific antibody constructs having a protein concentration of 1 mg/mL in the respective formulations. The first bispecific antibody construct (Construct A) had an intra-domain disulfide bridge on the binding domain, whereas the second bispecific antibody construct (Construct C) did not have an intra-domain disulfide bridge on the binding domain. Benzyl alcohol and citrate excipients were added to some of the samples, as shown in the table below.

| Sample | Effect of Excipient at 20° C. | Protein Concentration |
|---|---|---|
| Construct A | Control Sample | 1 mg/mL (500 μL) |
| Construct A + Benzyl Alcohol | Decreases aggregation | 1 mg/mL (500 μL) |
| Construct A + Citrate | Increases aggregation | 1 mg/mL (500 μL) |
| Construct C | Control Sample | 1 mg/mL (500 μL) |
| Construct C + Benzyl Alcohol | Increases aggregation | 1 mg/mL (500 μL) |

Figure 13:
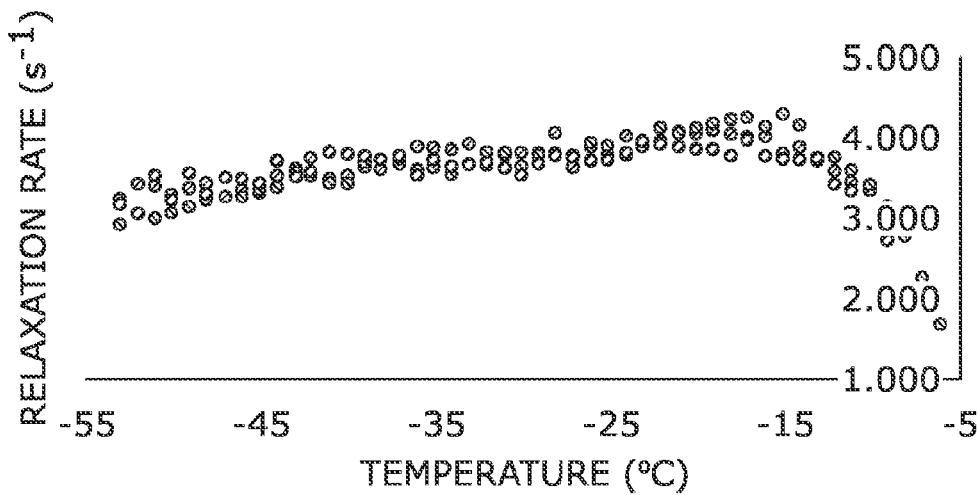
FIG. 13 shows the $R_1$ relaxation vs temperature curves for various bispecific antibody construct placebos at low temperatures. All three formulations had similar motions based on the relaxation rates regardless of the additional excipients.
Figure 14:
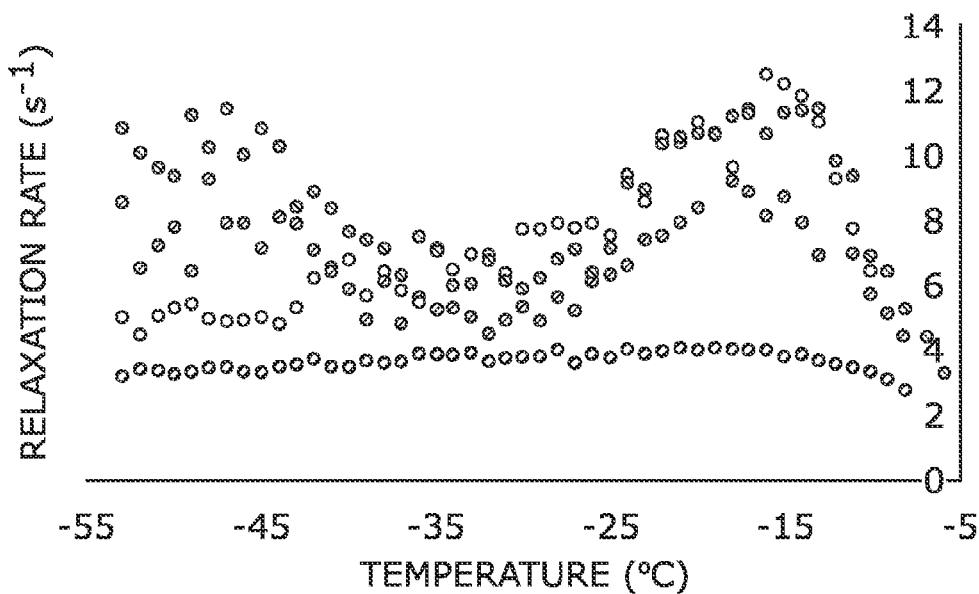
FIG. 14 shows the $R_1$ relaxation vs temperature curves for Construct A, demonstrating that benzyl alcohol ("BA") restricts motion of Construct A leading to less aggregation.
Figure 15:
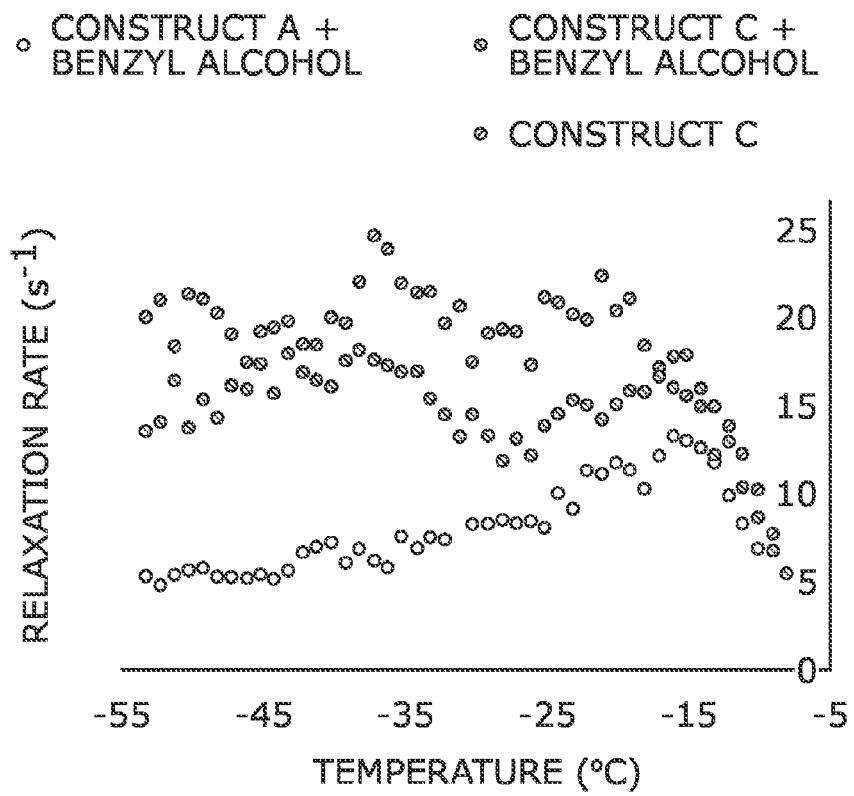
FIG. 15 shows the $R_1$ relaxation vs temperature curves for Construct A and Construct C demonstrating that benzyl alcohol ("BA") reduces aggregation in all bispecific antibody constructs except Construct C, indicating that the additional motion of the protein without the intra-domain disulfide bridge cannot be overcome.

Additional samples were prepared with additional bispecific antibody constructs and tested with benzyl alcohol and citrate. Three placebo formulations were also prepared: (a) a control placebo (no benzyl alcohol or citrate); (b) a placebo containing benzyl alcohol; and (c) a placebo containing citrate. The placebo formulations were identical to the test formulations except that they lacked the bispecific antibody construct. $R_1$ vs temperature was collected over the temperature range of about −55° C. to about 5° C. for all samples. The samples underwent a slow freeze from 0° C. to −53° C. by 1° C./min, and then relaxation was measured as the temperature was increased. As shown in FIG. 13, all three placebo formulations have similar motions based on the relaxation rates, regardless of the additional excipients. Further, all bispecific antibody constructs except Construct C demonstrated decreased −20° C. aggregation in the presence of benzyl alcohol. As shown in FIG. 14, the addition of benzyl alcohol resulted in restricted motion and decreased aggregation. Bispecific antibody constructs molecular motion in the platform and citrate formulations were similar. As shown in FIG. 15, Construct C had an overall relaxation rate that was much greater than Construct A. It is believed that the increase in aggregation of Construct C is due to the absence of the intra-domain disulfide bridge on the binding domain, and the presence of benzyl alcohol was unable to overcome the resulting motion.

Moreover, as shown in FIG. 18, the relaxation rate can be decreased by using a fast freeze (e.g., >10° C./min, or as fast as an instrument can go), indicating a reduction in molecular motion and aggregation, and an increase in the solid state stability of the formulation.

Thus, Example 6 shows how an excipient (e.g., benzyl alcohol) restricts motion in compounds (e.g., bispecific antibody constructs), leading to reduced aggregation. Example 6 further shows that stability in the frozen state can be increased by subjecting a formulation to a fast freeze, relative to the stability of the same formulation frozen using a slow freeze.

Example 7

Effect of Size on ssNMR Relaxation

Figure 16:
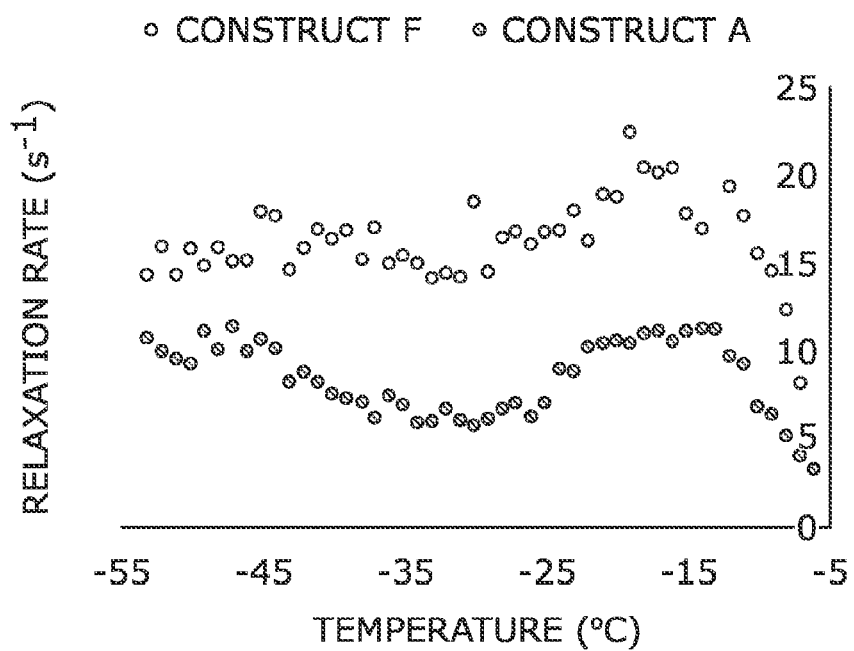
FIG. 16 shows the $R_1$ relaxation vs temperature curves for Construct F and Construct A, demonstrating the effect of size on ssNMR relaxation.

The effect of construct size on the ssNMR relaxation was shown using an antibody construct having a single binding domain (Construct F) and bispecific Construct A. Samples were prepared and $T_1$ vs relaxation data collected over the range of about −55° C. to about −5° C. Construct F, the smallest construct, was expected to have more motion and aggregation than the larger construct, Construct A. As shown in FIG. 16, the relaxation rate of Construct A was less than that of Construct F over the entire temperature range, indicating more molecular motion in the solid state.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A method of conducting direct detection $^1$H solid state NMR ("ssNMR") on a macromolecule-containing solid state formulation, the method comprising:
   (a) equilibrating a solid state formulation comprising a macromolecule at a first temperature;
   (b) conducting a $^1$H spin-lattice relaxation time ("$T_1$") experiment on the solid state formulation at the first temperature using direct detection $^1$H ssNMR to generate at least three free induction decay ("FID") plots at the first temperature, wherein the $T_1$ experiment comprises baseline suppression and a saturation recovery sequence having at least three variable delay times from which each FID plot is generated;
   (c) equilibrating the solid state formulation at a second temperature, and repeating step (b) at the second temperature to generate at least three FID plots at the second temperature;

(d) equilibrating the solid state formulation at a third temperature, and repeating step (b) at the third temperature to generate at least three FID plots at the third temperature;

(e) generating a saturation recovery curve at each temperature; and (f) fitting each saturation recovery curve to a nonlinear regression equation to generate a $T_1$ value at each temperature.

2. The method of claim 1, further comprising:

(g) converting each $T_1$ value to $^1$H spin-lattice relaxation rate ("$R_1$"), and (h) plotting $R_1$ versus temperature to generate a relaxation rate curve for the solid state formulation; and analyzing the relaxation rate curve to determine the molecular mobility of the macromolecule in the solid state formulation, the degree of aggregation in the solid state formulation, and/or the stability of the solid state formulation.

3. The method of claim 1, wherein the highest and lowest temperatures have a difference of at least about 25° C.

4. The method of claim 1, wherein said method excludes one or both of retuning and recalibrating the ssNMR probe after equilibrating at the first temperature.

5. The method of claim 1, wherein each $T_1$ experiment comprises at least five variable delay times at each temperature to generate at least five FID plots at each temperature.

6. The method of claim 1, wherein the saturation recovery curve is generated by:

(a) plotting the signal intensity of each of the at least three FID plots versus delay time; or (b) Fourier transforming each of the at least three FID plots to generate a plot of intensity versus frequency; and
 (i) plotting peak height versus delay time; or
 (ii) plotting integral peak intensity versus delay time.

7. The method of claim 1, wherein the $T_1$ experiment comprises magic angle spinning.

8. The method of claim 1, wherein all of the $T_1$ experiments are conducted within a time period of up to 48 hours.

9. The method of claim 1, wherein macromolecule is a biologic molecule.

10. The method of claim 1, wherein the solid state formulation is a lyophilized formulation and the fitting of step (f) is monoexponential.

11. The method of claim 10, wherein the highest and lowest temperatures have a difference of at least about 50° C.

12. The method of claim 10, wherein the $T_1$ experiment comprises a variable delay period in a range from about 0.01 seconds to about 60 seconds.

13. The method of claim 1, wherein the solid state formulation is a frozen formulation and the fitting of step (f) is biexponential.

14. The method of claim 13, wherein the highest and lowest temperatures have a difference of at least about 40° C.

15. The method of claim 13, wherein each $T_1$ experiment comprises nine variable delay times at each temperature to generate nine FID plots at each temperature.

16. The method of claim 13, wherein the $T_1$ experiment comprises a variable delay period in a range from about 0.1 seconds to about 240 seconds.

17. The method of claim 1, wherein the solid state formulation is a lyophilized formulation and:

the saturation recovery curve is generated by plotting the signal intensity of each of the at least three FID plots versus delay time;

the $T_1$ experiment comprises baseline suppression and magic angle spinning;

steps (d)-(f) are repeated at 15 or more temperatures;

each temperature is in a range from about −50° C. to about 150° C.;

the highest and lowest temperatures have a difference from about 75° C. to about 100° C.;

in each equilibrating step the solid state formulation is held at the temperature for a duration in the range of about one minute to about ten minutes before conducting the $T_1$ experiment;

the method excludes retuning and recalibrating the ssNMR probe after equilibrating at the first temperature;

the variable delay period is in a range from about 0.1 seconds to about 60 seconds; and each $T_1$ experiment comprises six variable delay times at each temperature to generate six FID plots at each temperature.

18. The method of claim 1, wherein the solid state formulation is a frozen formulation and:

the saturation recovery curve is generated by plotting the signal intensity of each of the at least three FID plots versus delay time;

the $T_1$ experiment comprises baseline suppression and magic angle spinning;

steps (d)-(f) are repeated at 25 or more temperatures;

each temperature is in a range from about −50° C. to about 0° C.;

the highest and lowest temperatures have a difference from about 25° C. to about 40° C.;

in each equilibrating step the solid state formulation is held at the temperature for a duration in the range of about one minute to about ten minutes before conducting the $T_1$ experiment;

the method excludes retuning and recalibrating the ssNMR probe after equilibrating at the first temperature;

the variable delay period is in a range from about 0.01 seconds to about 240 seconds; and each $T_1$ experiment comprises nine variable delay times at each temperature to generate nine FID plots at each temperature.

19. A method of selecting a macromolecule-containing solid state formulation among a group of test macromolecule-containing solid state formulations, the method comprising:

(I) generating a relaxation rate curve for each macromolecule-containing solid state formulation in the group of test macromolecule-containing solid state formulations; wherein the relaxation rate curve for each macromolecule-containing solid state formulation is generated by:

(a) equilibrating the solid state formulation at a first temperature;

(b) conducting a $^1$H spin-lattice relaxation time ("$T_1$") experiment on the solid state formulation at the first temperature using direct detection $^1$H ssNMR to generate at least three free induction decay ("FID") plots at the first temperature, wherein the $T_1$ experiment comprises baseline suppression and a saturation recovery sequence having at least three variable delay times from which each FID plot is generated;

(c) equilibrating the solid state formulation at a second temperature, and repeating step (b) at the second temperature to generate at least three FID plots at the second temperature;
(d) equilibrating the solid state formulation at a third temperature and repeating step (b) at the third temperature to generate at least three FID plots at the third temperature;
(e) generating a saturation recovery curve at each temperature;
(f) fitting each saturation recovery curve to a nonlinear regression equation to generate a $T_1$ value at each temperature;
(g) converting each $T_1$ value to $^1H$ spin-lattice relaxation rate ("$R_1$"), and
(h) plotting $R_1$ versus temperature to generate a relaxation rate curve for the solid state formulation;
(II) comparing the maximum $R_1$ peak value of each curve, the temperature of the maximum $R_1$ peak of each curve, the width of the maximum $R_1$ peak of each curve, or a combination thereof; and
(III) selecting the solid state formulation which has the lowest maximum $R_1$ peak value, the highest temperature of the maximum $R_1$ peak, or the narrowest $R_1$ peak width.

20. A method of selecting a formulation excipient for use in a macromolecule-containing solid state formulation, the method comprising:
(I) generating a relaxation rate curve for each macromolecule-containing solid state formulation in a group of test macromolecule-containing solid state formulations, each formulation having a different composition of excipients, a different amount of one or more excipients, or both; wherein the relaxation rate curve for each macromolecule-containing solid state formulation is generated by:

(a) equilibrating the solid state formulation at a first temperature;
(b) conducting a $^1H$ spin-lattice relaxation time ("$T_1$") experiment on the solid state formulation at the first temperature using direct detection $^1H$ ssNMR to generate at least three free induction decay ("FID") plots at the first temperature, wherein the $T_1$ experiment comprises baseline suppression and a saturation recovery sequence having at least three variable delay times from which each FID plot is generated;
(c) equilibrating the solid state formulation at a second temperature, and repeating step (b) at the second temperature to generate at least three FID plots at the second temperature;
(d) equilibrating the solid state formulation at a third temperature, and repeating step (b) at the third temperature to generate at least three FID plots at the third temperature;
(e) generating a saturation recovery curve at each temperature;
(f) fitting each saturation recovery curve to a nonlinear regression equation to generate a $T_1$ value at each temperature;
(g) converting each $T_1$ value to $^1H$ spin-lattice relaxation rate ("$R_1$"), and
(h) plotting $R_1$ versus temperature to generate a relaxation rate curve for the solid state formulation;
(II) comparing the maximum $R_1$ peak value of each curve, the temperature of the maximum $R_1$ peak of each curve, the width of the maximum $R_1$ peak of each curve, or a combination thereof; and
(III) selecting an excipient that is present in the solid state formulation that has the lowest maximum $R_1$ peak value, the highest temperature of the maximum $R_1$ peak, or the narrowest $R_1$ peak width.

* * * * *

UNITED STATES PATENT AND TRADEMARK OFFICE
CERTIFICATE OF CORRECTION

| | | |
|---|---|---|
| PATENT NO. | : 12,000,915 B2 | Page 1 of 1 |
| APPLICATION NO. | : 17/766055 | |
| DATED | : June 4, 2024 | |
| INVENTOR(S) | : Marc A. Caporini et al. | |

It is certified that error appears in the above-identified patent and that said Letters Patent is hereby corrected as shown below:

In the Claims

At Column 27, Line 15, "("$R_1$"), and" should be -- ("$R_1$"); and --.

At Column 28, Line 25, "("$R_1$"), and" should be -- ("$R_1$"); and --.

Signed and Sealed this
Eighteenth Day of February, 2025

Coke Morgan Stewart
*Acting Director of the United States Patent and Trademark Office*